United States Patent [19]

Ichijima et al.

[11] Patent Number: 5,071,735
[45] Date of Patent: Dec. 10, 1991

[54] SILVER HALIDE COLOR PHOTOGRAPHIC MATERIAL CONTAINING A COMPOUND RELEASING A DIR COMMAND UPON REACTION WITH AN OXIDIZED DEVELOPING AGENT

[75] Inventors: Seiji Ichijima; Yasuhiro Shimada, both of Kanagawa, Japan

[73] Assignee: Fuji Photo Film Co., Ltd., Kanagawa, Japan

[21] Appl. No.: 417,602

[22] Filed: Oct. 5, 1989

[30] Foreign Application Priority Data

Oct. 6, 1988 [JP] Japan .................. 63-252481

[51] Int. Cl.$^5$ .................. G03C 1/34; G03C 7/305
[52] U.S. Cl. .................. 430/505; 430/544; 430/548; 430/553; 430/555; 430/557; 430/558; 430/957
[58] Field of Search .............. 430/505, 544, 957, 548, 430/553, 555, 557, 558

[56] References Cited

U.S. PATENT DOCUMENTS

| 4,338,393 | 7/1982 | Bailey et al. | 430/386 |
| 4,438,193 | 3/1984 | Uemura et al. | 430/505 |
| 4,618,571 | 10/1986 | Ichijima et al. | 430/505 |
| 4,737,451 | 4/1988 | Ichijima | 430/544 |
| 4,770,982 | 9/1988 | Ichijima et al. | 430/505 |
| 4,927,743 | 5/1990 | Tamoto | 430/505 |

FOREIGN PATENT DOCUMENTS

| 0200878 | 11/1986 | European Pat. Off. | 430/544 |
| 0160954 | 9/1983 | Japan | 430/544 |
| 60-203943 | 10/1985 | Japan . | |
| 61-113060 | 5/1986 | Japan . | |
| 61-233741 | 10/1986 | Japan . | |
| 61-238057 | 10/1986 | Japan . | |
| 62-291645 | 12/1987 | Japan . | |
| 1243058 | 9/1989 | Japan | 430/544 |

OTHER PUBLICATIONS

Patent Abstracts of Japan, vol. 101, No. 298 (P-505)(2354) Oct. 9, 1986 abstracting JP-A-6-1-113060.

Primary Examiner—Charles L. Bowers, Jr.
Assistant Examiner—Lee C. Wright
Attorney, Agent, or Firm—Sughrue, Mion, Zinn, Macpeak & Seas

[57] ABSTRACT

A silver halide color photographic material comprising a support having thereon at least one silver halide emulsion layer, wherein the silver halide color photographic material contains a compound represented by the following general formula (I):

$$A—(L)_l—B \qquad (I)$$

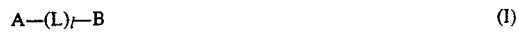

wherein A represents a group whose bond to (L)$_l$—B is capable of being cleaved upon reaction with an oxidation product of a developing agent; L represents a group whose bond to B is capable of being cleaved after being cleaved from A; B represents a 5-membered, 6-membered or 7-membered nitrogen-containing unsaturated heterocyclic grop which has 2 to 6 carbon atoms, which is connected to A-(L)$_l$ at the nitrogen atom, and which has a sulfonamido group and a development inhibitor group or a precursor thereof on the ring carbon atoms; l represents an integer of 0 to 2, and when l represents 2, the two L's may be the same or different. The silver halide color photographic material has excellent sharpness and color reproducibility.

19 Claims, No Drawings

SILVER HALIDE COLOR PHOTOGRAPHIC MATERIAL CONTAINING A COMPOUND RELEASING A DIR COMMAND UPON REACTION WITH AN OXIDIZED DEVELOPING AGENT

FIELD OF THE INVENTION

The present invention relates to a silver halide color photographic material, and more particularly to a silver halide color photographic material which has excellent sharpness and color reproducibility.

BACKGROUND OF THE INVENTION

In the field of color photographic light-sensitive materials, couplers which are capable of releasing a development inhibitor (DIR couplers) have been hitherto employed for the purpose of improving sharpness and color reproducibility. The improvement in color image quality using DIR couplers is marked and various kinds of DIR couplers have been developed and proposed.

One example of a DIR coupler is a coupler which is capable of releasing a development inhibitor at the coupling position as described, for example, in U.S. Pat. Nos. 3,227,554, 3,148,062, 3,933,500 and 4,477,563.

Since a development inhibitor is connected to the coupling position in this type of DIR coupler, a problem exists in that the coupling reaction of the coupler with the oxidation product of the developing agent is delayed in case of using some type of development inhibitors. In order to solve this problem, interposing a linking group between the coupling position of the coupler and the development inhibitor has been proposed. Examples of such couplers are described, for example in U.S. Pat. Nos. 4,146,396, 4,248,962 and 4,421,845. With these couplers, a certain improvement in the coupling reaction speed is observed and the performance is somewhat improved. However, it has been found that the coupling reaction speed obtained is not greatly different from that of the DIR coupler wherein a development inhibitor is directly connected to the coupling position and which has originally a high reactivity with the oxidation product of a developing agent.

Further, couplers capable of releasing a DIR coupler are described, for example, in U.S. Pat. Nos. 4,438,193 and 4,338,393, JP-A-62-291645 and JP-A-60-203943 (the term "JP-A" as used herein means an "unexamined published Japanese patent application"). Although these couplers exhibit some degree of improvement in graininess or sharpness, further improvement is desired. In addition, with respect to color reproducibility it has been found that a problem may occur in that a dye formed upon a reaction of a DIR coupler released and diffused with the oxidation product of developing agent partially remains in the photographic material.

Moreover, other types of couplers are known and described, for example, in U.S. Pat. Nos. 4,618,571 and 4,737,451, JP-A-61-233741 and JP-A-61-238057. These couplers are one kind of DIR couplers because they release a compound which is capable of releasing a development inhibitor through an oxidation reduction reaction (DIR redox compound). These couplers exhibit excellent improvement in sharpness due to an edge effect and in color reproducibility due to an interlayer effect without the above described problems. However, these couplers are expensive to produce them and are restricted in practical use, thus further improvement has been desired.

SUMMARY OF THE INVENTION

Therefore, an object of the present invention is to provide a silver halide color photographic material which has excellent sharpness and color reproducibility using a DIR compound which can be produced at a suitable cost and can be used in a sufficiently large amount.

This and other objects of the present invention will become apparent from the following detailed description and examples.

The above-described objects of the present invention are accomplished by a silver halide color photographic material comprising a support having thereon at least one silver halide emulsion layer, wherein the silver halide color photographic material contains a compound represented by the following general formula (I):

$$A\text{—}(L)_l\text{—}B \qquad (I)$$

wherein A represents a group whose bond to $(L)_l$—B is capable of being cleaved upon reaction with an oxidation product of a developing agent; L represents a group whose bond to B is capable of being cleaved after being cleaved from A; B represents a 5-membered, 6-membered or 7-membered nitrogen-containing unsaturated heterocyclic group which has 2 to 6 carbon atoms, which is connected to A—$(L)_l$ at the nitrogen atom, and which has a sulfonamido group and a development inhibitor group or a precursor thereof on the ring carbon atoms; l represents an integer of 0 to 2, and when l represents 2, the two L's may be the same or different.

DETAILED DESCRIPTION OF THE INVENTION

The compound represented by the general formula (I) is explained in greater detail below.

In the general formula (I), A represents a coupler residue or an oxidation-reduction group which is capable of releasing $(L)_l$—B upon oxidation. L in the general formula (I) is a conventional timing group or linking group. The group represented by B is a group capable of being oxidized by the oxidation product of a developing agent after being released from A—$(L)_l$ at the time of development. More specifically, the sulfonamido group thereon is oxidized to a sulfonylimino group whereby a development inhibitor is cleaved for the first time.

The compounds represented by the general formula (I) include those represented by the following general formula (II):

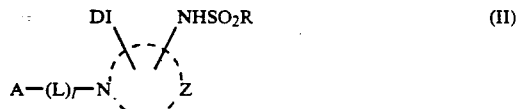

wherein A, L and l each has the same meaning as defined in the general formula (I); Z represents an atomic group necessary to form a 5-membered, 6-membered or 7-membered nitrogen-containing unsaturated heterocyclic ring containing 2 to 6 carbon atoms together with the nitrogen atom; DI represents a development inhibitor group; and R represents a substituent; and DI is connected to a carbon atom of the heterocyclic ring represented by Z through a hetero atom included therein, and the sulfonamido group is connected to a carbon atom of the heterocyclic ring represented by Z, provided that the nitrogen atom at which A—(L)$_l$ is connected and the nitrogen atom in the sulfonamido group are positioned so as to satisfy the Kendall-Pelz rule as described, for example, in T. H. James ed., "The Theory of the Photographic Process", 4th ed., pp. 298-325, Macmillan Publishing Co., Inc., New York, 1977.

While not desiring to be bound, the reaction process for releasing a development inhibitor upon the reaction of the compound represented by the general formula (II) with the oxidation product of a developing agent at the time of development may be presumed to proceed in accordance with the following scheme:

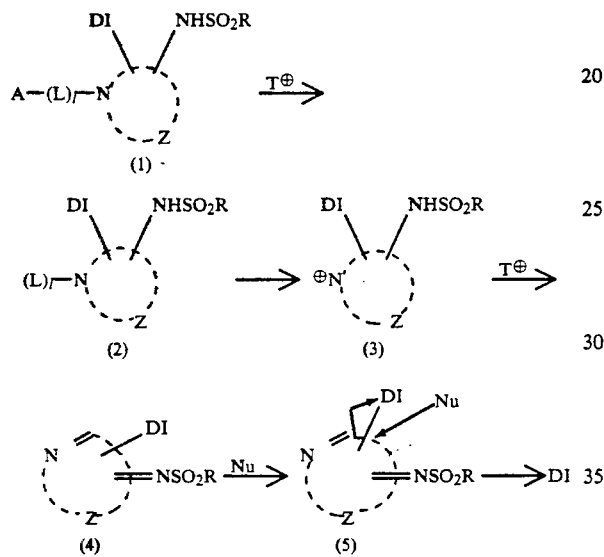

In the above scheme, A, L, l, Z, DI and R each has the same meaning as defined in the general formula (II) above; T$^\oplus$ represents an oxidation product of a developing agent; and Nu represents a nucleophilic reagent, for example, hydroxylamine, a sulfite ion or a hydroxy ion, present at the time of development.

The reaction of (3) to (4) is an oxidation-reduction reaction, and the reaction of (5) to release DI is, for example, a nucleophilic addition-elimination reaction.

Suitable examples of coupler residues represented by A include a yellow coupler residue (for example, an open-chain ketomethylene type coupler residue such as acylacetanilide or malondianilide), a magenta coupler residue (for example, a 5-pyrazolone type coupler residue, a pyrazolotriazole type coupler residue or a pyrazoloimidazole type coupler residue), a cyan coupler residue (for example, a phenol type coupler residue, a naphthol type coupler residue or an imidazole type coupler residue as described in EP-A-249453), and a non-color forming coupler residue (for example, an indanone type coupler residue or an acetophenone type coupler residue). Further, the heterocyclic type coupler residues as described in U.S. Pat. Nos. 4,315,070, 4,183,752, 4,174,969, 3,961,959 and 4,171,223 are also useful.

When A represents an oxidation-reduction group, the oxidation-reduction group is a group capable of being cross-oxidized by the oxidation product of a developing agent. Suitable examples thereof include a hydroquinone, a catechol, a pyrogallol, a 1,4-naphthohydroquinone, a 1,2-naphthohydroquinone, a sulfonamidophenol, a hydrazide and a sulfonamidonaphthol. Specific examples of these groups are described, for example, in JP-A-61-230135, JP-A-62-251746, JP-A-61-278852, U.S. Pat. Nos. 3,364,022, 3,379,529, 3,639,417 and 4,684,604, and J. Org. Chem., Vol. 29, page 588 (1964).

In the general formula (I) or (II), A preferably represents a coupler residue.

Where A represents a coupler residue in the general formula (I) or (II), preferred coupler residues include those represented by the general formula (Cp-1), (Cp-2), (Cp-3), (Cp-4), (Cp-5), (Cp-6), (Cp-7), (Cp-8), (Cp-9) or (Cp-10) described below. These coupler residues are preferred because of their high coupling rates.

-continued

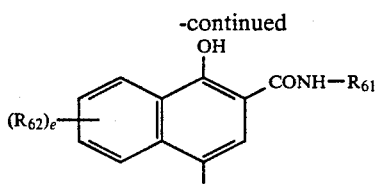 (Cp-8)

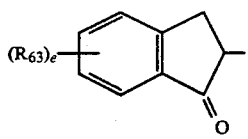 (Cp-9)

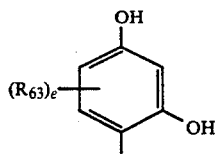 (Cp-10)

In the above-described general formulae, the free bond shown attached to the coupling position indicates a position to which a group capable of being released upon coupling is bonded. When $R_{51}$, $R_{52}$, $R_{53}$, $R_{54}$, $R_{55}$, $R_{56}$, $R_{57}$, $R_{58}$, $R_{59}$, $R_{60}$, $R_{61}$, $R_{62}$, or $R_{63}$ in the above-described general formulae contains a diffusion-resistant group, the total number of carbon atoms included therein is from 8 to 40 and preferably from 10 to 30. In other cases, the total number of carbon atoms included therein is preferably not more than 15. In cases of bis type, telomer type or polymer type couplers, any of the above-described substituents forms a divalent group and may connect to a repeating unit, etc. In such cases, the total number of carbon atoms can be outside of the above-described range.

$R_{51}$ to $R_{63}$, d and e in the above-described general formulae (Cp-1) to (Cp-10) are explained in detail below.

More specifically, $R_{41}$ represents an aliphatic group, an aromatic group or a heterocyclic group; $R_{42}$ represents an aromatic group or a heterocyclic group; and $R_{43}$, $R_{44}$ and $R_{45}$ each represents a hydrogen atom, an aliphatic group, an aromatic group or a heterocyclic group.

$R_{51}$ represents a group as defined for $R_{41}$.

$R_{52}$ and $R_{53}$ each represents a group as defined for $R_{42}$.

$R_{54}$ represents a group as defined for $R_{41}$, a group

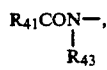

a group

a group

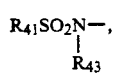

a group $R_{41}S-$, a group $R_{43}O-$, a group

or a group $N\equiv C-$.

$R_{55}$ represents a group as defined for $R_{41}$.

$R_{56}$ and $R_{57}$ each represents a group as defined for $R_{43}$, a group $R_{41}S-$, a group $R_{43}O-$, a group

or a group

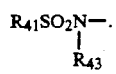

$R_{58}$ represents a group as defined for $R_{41}$.

$R_{59}$ represents a group as defined for $R_{41}$, a group

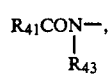

a group

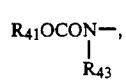

a group

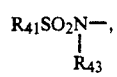

a group

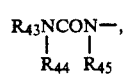

a group $R_{41}O-$, a group $R_{41}S-$, a halogen atom or a group

d represents an integer from 0 to 3. When d represents 2 or more, the two or more $R_{59}$'s may be the same or different. Further, each of the two $R_{59}$'s may be a divalent group and connected with each other to form a cyclic structure.

Representative examples of divalent groups for forming a cyclic structure include a group

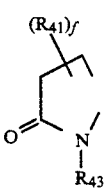

or a group

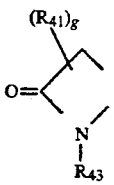

wherein f represents an integer from 0 to 4; and g represents an integer from 0 to 2.

$R_{60}$ represents a group as defined for $R_{41}$.

$R_{61}$ represents a group as defined for $R_{41}$.

$R_{62}$ represents a group as defined for $R_{41}$, a group $R_{41}CONH-$, a group $R_{41}OCONH-$, a group $R_{41}SO_2NH-$, a group

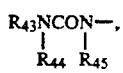

a group

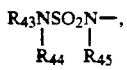

a group $R_{43}O-$, a group $R_{41}S-$, a halogen atom or a group

$R_{63}$ represents a group as defined for $R_{41}$, a group

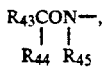

a group

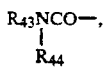

a group

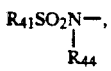

a group

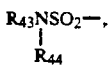

a group $R_{41}SO_2-$, a group $R_{43}OCO-$, a group $R_{43}OSO_2-$, a halogen atom, a nitro group, a cyano group or a group $R_{43}CO-$.

e represents an integer from 0 to 4. When e represents 2 or more, the two or more $R_{62}$'s or $R_{63}$'s may be the same or different.

The aliphatic group described above is an aliphatic hydrocarbon group having from 1 to 32 carbon atoms, preferably from 1 to 22 carbon atoms and may be saturated or unsaturated, a straight chain, branched chain or cyclic, or substituted or unsubstituted. Representative examples of aliphatic group include a methyl group, an ethyl group, a propyl group, an isopropyl group, a butyl group, a tert-butyl group, an isobutyl group a tert-amyl group, a hexyl group, a cyclohexyl group, a 2-ethylhexyl group, an octyl group, a 1,1,3,3-tetramethylbutyl group, a decyl group, a dodecyl group, a hexadecyl group, and an octadecyl group.

The aromatic group described above is an aromatic group having from 6 to 20 carbon atoms, and preferably is an unsubstituted or substituted phenyl group or an unsubstituted or substituted naphthyl group.

The heterocyclic group described above is a heterocyclic group having from 1 to 20 carbon atoms, preferably from 1 to 7 carbon atoms, and containing at least one of a nitrogen atom, an oxygen atom and a sulfur atom, as a hetero atom, and preferably is a three-membered to eight-membered, substituted or unsubstituted heterocyclic group. Representative examples of the unsubstituted heterocyclic group include a 2-pyridyl group, a 2-thienyl group, a 2-furyl group, a 1-imidazolyl group, a 1-indolyl group, a phthalimido group, a 1,3,4-thiadiazol-2-yl group, a 2-quinolyl group, a 2,4-dioxo-1,3-imidazolidin-5-yl group, a 2,4-dioxo-1,3-imidazolidin-3-yl group, a succinimido group, a 1,2,4-triazol-2-yl group, and a 1-pyrazolyl group.

The aliphatic group, aromatic group and heterocyclic group may have one or more substituents as described above. Representative examples of suitable substituents include a halogen atom, a group $R_{47}O-$, a group $R_{46}S-$, a group

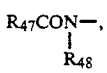

a group

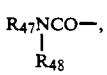

a group

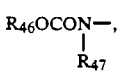

a group

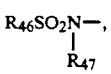

a group

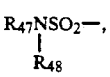

a group $R_{46}SO_2-$, a group $R_{47}OCO-$, a group

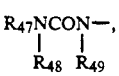

a group as defined for $R_{46}$, a group

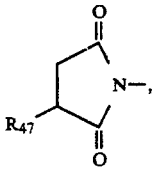

a group $R_{46}COO-$, a group $R_{47}OSO_2-$, a cyano group, or a nitro group. In the above described formulae, $R_{46}$ represents an aliphatic group, an aromatic group or a heterocyclic group; and $R_{47}$, $R_{48}$ and $R_{49}$ each represents a hydrogen atom, an aliphatic group, an aromatic group or a heterocyclic group. The aliphatic group, aromatic group and heterocyclic group each has the same meaning as defined above.

Preferred embodiments with respect to $R_{51}$ to $R_{63}$, d and e are described below.

$R_{51}$ preferably is an aliphatic group or an aromatic group.

$R_{52}$, $R_{53}$ and $R_{55}$ each is preferably an aromatic group.

$R_{54}$ is preferably a group $R_{41}CONH-$ or a group

$R_{56}$ and $R_{57}$ each is preferably an aliphatic group, a group $R_{41}O-$ or a group $R_{41}S-$.

$R_{58}$ is preferably an aliphatic group or an aromatic group.

$R_{59}$ in the general formula (Cp-6) is preferably a chlorine atom, an aliphatic group or a group $R_{41}CONH-$.

d in the general formula (Cp-6) is preferably 1 or 2.

$R_{60}$ is preferably an aromatic group.

$R_{59}$ in the general formula (Cp-7) is preferably a group $R_{41}CONH-$.

d in the general formula (Cp-7) is preferably 1.

$R_{61}$ is preferably an aliphatic group or an aromatic group.

e in the general formula (Cp-8) is preferably 0 or 1.

$R_{62}$ is preferably a group $R_{41}OCONH-$, a group $R_{41}CONH-$ or a group $R_{41}SO_2NH-$. The position of $R_{62}$ is preferably the 5-position of the naphthol ring.

$R_{63}$ in the general formula (Cp-9) is preferably a group $R_{41}CONH-$, a group $R_{41}SO_2NH-$, a group

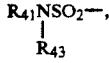

a group $R_{41}SO_2-$, a group

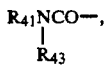

a nitro group or a cyano group.

$R_{63}$ in the general formula (Cp-10) is preferably a group

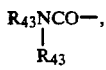

a group $R_{43}OCO-$ or a group $R_{43}CO-$.

Representative examples of $R_{51}$ to $R_{63}$ are set forth below.

Examples of $R_{51}$ include a tert-butyl group, a 4-methoxyphenyl group, a phenyl group, a 3-{2-(2,4-di-tert-amylphenoxy)butanamido}phenyl group, or a methyl group.

Examples of $R_{52}$ and $R_{53}$ include a 2-chloro-5-dodecyloxycarbonylphenyl group, a 2-chloro-5-hexadecylsulfonamidophenyl group, a 2-chloro-5-tetradecanamidophenyl group, a 2-chloro-5-{4-(2,4-di-tert-amylphenoxy)-butanamido}phenyl group, a 2-chloro-5-{2-(2,4-di-tert-amylphenoxy)butanamido}phenyl group, 2-methoxyphenyl group, a 2-methoxy-5-tetradecyloxycarbonylphenyl group, a 2-chloro-5-(1-ethoxycarbonylethoxycarbonyl)phenyl group, a 2-pyridyl group, a 2-chloro-5-octyloxycarbonyl phenyl group, a 2,4-dichlorophenyl group, a 2-chloro-5-(1-dodecyloxycarbonylethoxycarbonyl)phenyl group, a 2-chlorophenyl group, or a 2-ethoxyphenyl group.

Examples of $R_{54}$ include a 3-{2-(2,4-di-tert-amylphenoxy)butanamido}benzamido group, a 3-{4-(2,4-di-tert-amylphenoxy)butanamido}benzamido group, a 2-chloro-5-tetradecanamidoanilino group, a 5-(2,4-di-tert-amylphenoxyacetamido)benzamido group, a 2-chloro-5-dodecenyl-succinimidoanilino group, a 2-chloro-5-{2-(3-tert-butyl-4-hydroxyphenoxy)tetradecanamido}anilino group, a 2,2-dimethylpropanamido group, a 2-(3-pentadecylphenoxy)butanamido group, a pyrrolidino group, or an N,N-dibutylamino group.

Examples of $R_{55}$ include a 2,4,6-trichlorophenyl group, a 2-chlorophenyl group, a 2,5-dichlorophenyl group, a 2,3-dichlorophenyl group, a 2,6-dichloro-4-methoxyphenyl group, a 4-{2-(2,4-di-tert-amylphenoxy)-butanamido}phenyl group, or a 2,6-dichloro-4-methanesulfonylphenyl group.

Examples of $R_{56}$ include a methyl group, an ethyl group, an isopropyl group, a methoxy group, an ethoxy group, a methylthio group, an ethylthio group, a 3-phenylureido group, or a 3-(2,4-di-tert-amylphenoxy)-propyl group.

Examples of $R_{57}$ include a 3-(2,4-di-tert-amylphenoxy)propyl group, a 3-[4-{2-[4-(4-hydroxyphenylsulfonyl)phenoxy]tetradecanamido}phenyl]propyl group, a methoxy group, a methylthio group, an ethylthio group, a methyl group, a 1-methyl-2-{2-octyloxy-5-[2-octyloxy-5-(1,1,3,3-tetramethylbutyl)phenylsulfonamido]phenylsulfonamido}ethyl group, a 3-{4-(4-dodecyloxyphenylsulfonamido)phenyl}propyl group, a 1,1-dimethyl-2-[2-octyloxy-5-(1,1,3,3-tetramethylbutyl)phenylsulfonamido]-ethyl group, or a dodecylthio group.

Examples of $R_{58}$ include a 2-chlorophenyl group, a pentafluorophenyl group, a heptafluoropropyl group, a 1-(2,4-di-tert-amylphenoxy)propyl group, a 3-(2,4-di-tert-amylphenoxy)propyl group, a 2,4-di-tert-amylmethyl group, or a furyl group.

Examples of $R_{59}$ include a chlorine atom, a methyl group, an ethyl group, a propyl group, a butyl group, an isopropyl group, a 2-(2,4-di-tert-amylphenoxy)-butanamido group, a 2-(2,4-di-tert-amylphenoxy)-hexanamido group, a 2-(2,4-di-tert-octylphenoxy)octanamido group, a 2-(2-chlorophenoxy)tetradecanamido group, a 2-{4-(4-hydroxyphenylsulfonyl)phenoxy}tetradecanamido group, or a 2-{2-(2,4-di-tert-amylphenoxyacetamido)-phenoxy}butanamido group.

Examples of $R_{60}$ include a 4-cyanophenyl group, 2-cyanophenyl group, a 4-butylsulfonylphenyl group, a 4-propylsulfonylphenyl group, a 4-chloro-3-cyanophenyl group, a 4-ethoxycarbonylphenyl group, or a 3,4-dichlorophenyl group.

Examples of $R_{61}$ include a dodecyl group, a hexadecyl group, a cyclohexyl group, a 3-(2,4-di-tert-amylphenoxy)propyl group, a 4-(2,4-di-tert-amylphenoxy)butyl group, a 3-dodecyloxypropyl group, a tert-butyl group a 2-methoxy-5-dodecyloxycarbonylphenyl group, or a 1-naphthyl group.

Examples of $R_{62}$ include an isobutyloxycarbonylamino group, an ethoxycarbonylamino group, a phenylsulfonylamino group, a methanesulfonamido group, a benzamido group, a trifluoroacetamido group, a 3-phenylureido group, a butoxycarbonylamino group, or an acetamido group.

Examples of $R_{63}$ include a 2,4-di-tert-amylphenoxyacetamido group, a 2-(2,4-di-tert-amylphenoxy)butanamido group, a hexadecylsulfonamido group, an N-methyl-N-octadecylsulfamoyl group, an N,N-dioctylsulfamoyl group, a 4-tert-octylbenzoyl group, a dodecyloxycarbonyl group, a chlorine atom, a nitro group, a cyano group, an N-{4-(2,4-di-tert-amylphemoxy)butyl}-carbamoyl group, an N-3-(2,4-di-tert-amylphenoxy)propylsulfamoyl group, a methanesulfonyl group, or a hexadecylsulfonyl group.

The linking group represented by L in the general formula (I) or (II) includes, for example, a group utilizing a cleavage reaction of a hemiacetal as described, for example, in U.S. Pat. Nos. 4,146,396, 4,652,516 and 4,698,297, a timing group undergoing a cleavage reaction utilizing an intramolecular nucleophilic reaction as described, for example, in U.S. Pat. No. 4,248,962, a timing group undergoing a cleavage reaction utilizing an electron transfer reaction as described, for example, in U.S. Pat. Nos. 4,409,323 and 4,421,845, a group undergoing a cleavage reaction utilizing a hydrolysis reaction of an iminoketal as described, for example, in U.S. Pat. No. 4,546,073, and a group undergoing a cleavage reaction utilizing a hydrolysis reaction of an ester as described, for example, in West German Patent Application (OLS) No. 2,626,317.

Two or more of these groups may be employed in a combination.

L is connected to A through a hetero atom, preferably an oxygen atom, a sulfur atom or a nitrogen atom, included therein.

Preferred examples of linking groups represented by L include a methyleneoxy group, a 4-methylene-3-pyrazolyloxy group, a 2- or 4-methylenephenoxy group or a 2-carbonylaminomethylphenoxy group. In such cases, L is connected to A in the general formula (I) or (II) through the oxygen atom thereof.

The divalent linking group may have one or more substituents on positions capable of being substituted (for example, a methylene group or a benzene ring). Representative examples of suitable substituents include an alkyl group (for example, methyl, ethyl, isopropyl, dodecyl), an acyl group (for example, benzoyl, acetyl), an alkoxy group (for example, methoxy, ethoxy), an alkoxycarbonyl group (for example, methoxycarbonyl, butoxycarbonyl), a carbamoyl group (for example, ethylcarbamoyl), a nitro group, a carboxy group, a sulfonyl group (for example, methanesulfonyl), an aryl group (for example, 4-nitrophenyl, 4-carboxyphenyl), a halogen atom (for example, chlorine, fluorine), and a sulfamoyl group (for example, octadecylsulfamoyl).

The substituent represented by R in the general formula (II) is preferably an aliphatic group, an aromatic group, a heterocyclic group, an aliphatic oxy group, or an amino group (including an unsubstituted amino group, an aliphatic amino group and an aromatic amino group). The aliphatic group, aromatic group and heterocyclic group each has the same meaning as defined for $R_{41}$ above.

Particularly preferred groups for R are an aliphatic group or an aromatic group.

Suitable examples of heterocyclic rings formed by Z together with the nitrogen atom include a pyrrole ring, an imidazole ring, a pyrazole ring, an 1,2,4-triazole ring, an indole ring or an α-pyridone ring. The heterocyclic ring is connected to $A-(L)_l$ at the nitrogen atom formed by eliminating a hydrogen atom from

and connected to DI and $NHSO_2R$ at the carbon atoms formed by eliminating the hydrogen atoms from two methine groups, respectively. The heterocyclic ring may further have one or more substituents on positions capable of being substituted. Examples of suitable substituents include those illustrated for the heterocyclic group represented by $R_{41}$ above. It is preferred, however, that a hydroxy group is eliminated from the substituents.

Development inhibitor groups represented by DI in the general formula (II) specifically include a heterocyclic thio group and a nitrogen-containing heterocyclic group connected through the nitrogen atom therein. Specific examples thereof include a tetrazolylthio group, a thiadiazolylthio group, an oxadiazolylthio group, a triazolylthio group, a benzimidazolylthio group, a benzothiazolylthio group, a tetrazolylseleno group, a benzoxazolylthio group, a benzotriazolyl group, a triazolyl group, or a benzimidazolyl group. These groups are described, for example, in U.S. Pat. Nos. 3,227,554, 3,384,657, 3,615,506, 3,617,291, 3,733,201, 3,933,500, 3,958,993, 3,961,959, 4,149,886, 4,259,437, 4,095,984 and 4,477,563, and British Patent 1,450,479.

Of the compounds represented by the general formula (II), preferred compounds are those represented by the following general formula (III):

wherein A, L, l, DI and R each has the same meaning as defined in the general formula (I) or (II); one of $Z_1$, $Z_2$, $Z_3$ and $Z_4$ represents a carbon atom connected to DI; one of $Z_1$, $Z_2$, $Z_3$ and $Z_4$ other than the methine group connected to DI represents a carbon atom connected to $NHSO_2R$; and the two remaining $Z_1$, $Z_2$, $Z_3$ and $Z_4$ each represents a substituted or unsubstituted methine group or a nitrogen atom.

In the general formula (III), when $Z_1$, $Z_2$, $Z_3$ or $Z_4$ represents a substituted methine group other than the methine group having DI or $NHSO_2R$ as the substituent, representative substituents therefor include an aliphatic group (preferably having from 1 to 16 carbon atoms, and including, for example, methyl, ethyl, propyl, 2-hydroxyethyl, isopropyl, tert-butyl, cyclohexyl), an aromatic group (preferably having from 6 to 10 carbon atoms, and including, for example, phenyl, 2-chlorophenyl, 2-acetamidophenyl, 4-methoxyphenyl), a halogen atom (for example, chlorine, fluorine, bromine), an alkoxy group (preferably having from 1 to 16 carbon atoms, and including, for example, methoxy, ethoxy, 2-methoxyethoxy, 2-sulfonamidoethoxy), an alkylthio group (preferably having from 1 to 16 carbon atoms, and including, methylthio, ethylthio, propylthio, octylthio), an aromatic thio group (preferably having from 6 to 16 carbon atoms, and including, for example, phenylthio, 4-tert-buthylphenylthio, 4-chlorophenylthio, 4-methylphenylthio), a sulfonyl group (preferably having from 1 to 16 carbon atoms, and including, for example, methanesulfonyl, buthanesulfonyl, benzenesulfonyl, octanesulfonyl), an alkoxycarbonyl group (preferably having from 2 to 16 carbon atoms, and including, for example, methoxycarbonyl, buthoxycarbonyl), an acylamino group (preferably having from 2 to 16 carbon atoms, and including, for example, acetamido, butanamido, benzamido, octanamido), an acyl group (preferably having from 2 to 16 carbon atoms, and including, for example, acetyl, benzoyl), a carbamoyl group (preferably having from 1 to 16 carbon atoms, and including, for example, unsubstituted carbamoyl, N-ethylcarbamoyl, N-phenylcarbamoyl), a ureido group (preferably having from 1 to 16 carbon atoms, and including, for example, 3-phenylureido, 3-butylureido), a sulfamoyl group (preferably having up to 16 carbon atoms, and including, for example, N,N-diethylsulfamoyl, N-phenylsulfamoyl), an amino group (preferably having up to 16 carbon atoms, and including, for example, N,N-diethylamino, anilino), a sulfonamido group (preferably having from 1 to 16 carbon atoms, and including, for example, methanesulfonamido, benzenesulfonamido), and a carboxy group.

The compound according to the present invention can be employed in a multilayer multicolor photographic material comprising a support having thereon at least three light-sensitive layers having spectral sensitivity different from each other for the main purpose of improving sharpness, color reproducibility or graininess. A multilayer natural color photographic material generally includes at least one red-sensitive silver halide emulsion layer, at least one green-sensitive silver halide emulsion layer and at least one blue-sensitive silver halide emulsion layer, respectively, on a support. The order of the layers can be appropriately varied, if desired. The compound according to the present invention can be present in any appropriate layer including not only a light-sensitive emulsion layer but also a layer adjacent thereto, for example, an intermediate layer. Further, the compound according to the present invention can be present in any light-sensitive layer of appropriate sensitivity, for example, a high-sensitive layer or a low-sensitive layer.

The amount of the compound according to the present invention employed can be varied depending on the structure of the compound. However, a preferred amount is in the range from $1 \times 10^{-6}$ mol to 0.5 mol, particularly from $1 \times 10^{-5}$ mol to $1 \times 10^{-1}$ mol per mol of silver present in the same layer in which it is present or a layer adjacent thereto.

The compound according to the present invention can be employed in a combination with a color image forming coupler. In such a case, a molar ratio of the compound according to the present invention/color image forming coupler is generally from 0.01/99.99 to 50/50, preferably from 1/99 to 30/70.

Specific examples of the compounds according to the present invention are set forth below, but the present invention should not be construed as being limited thereto.

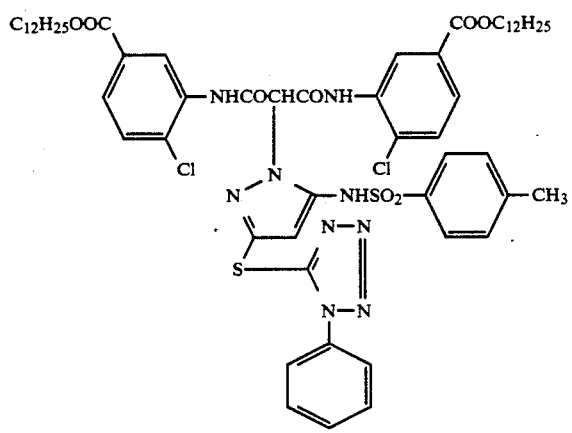

(1)

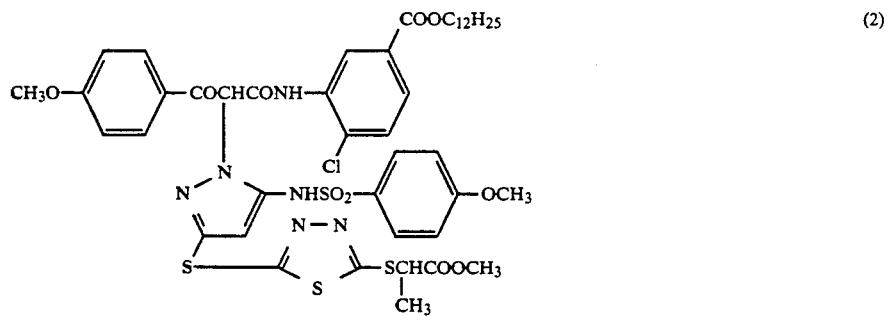
(2)
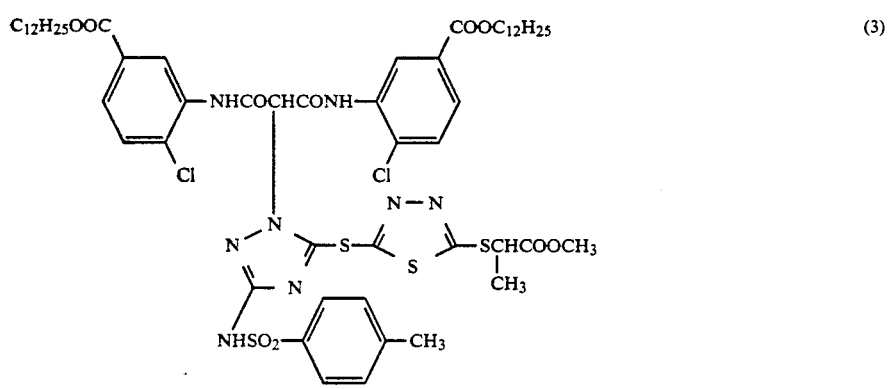
(3)
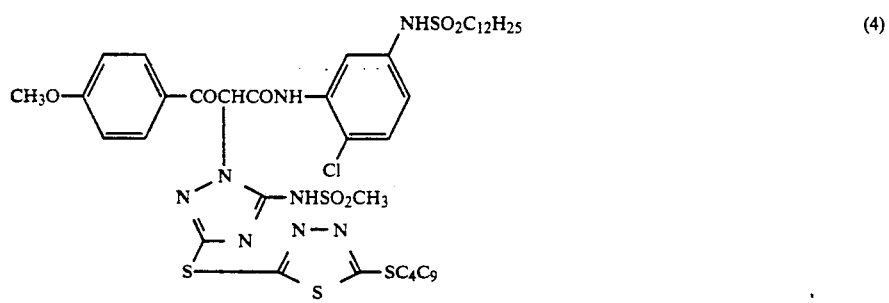
(4)
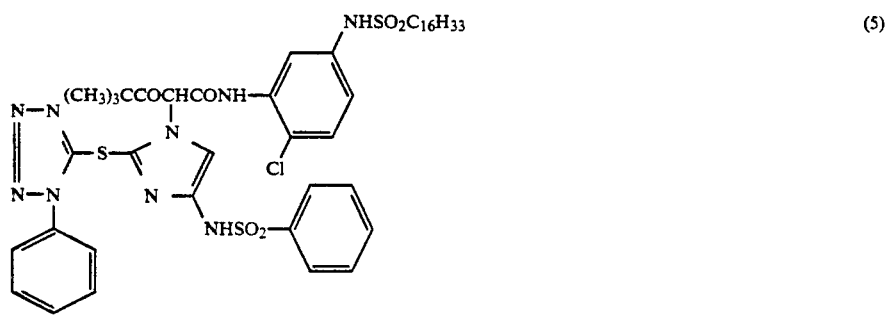
(5)

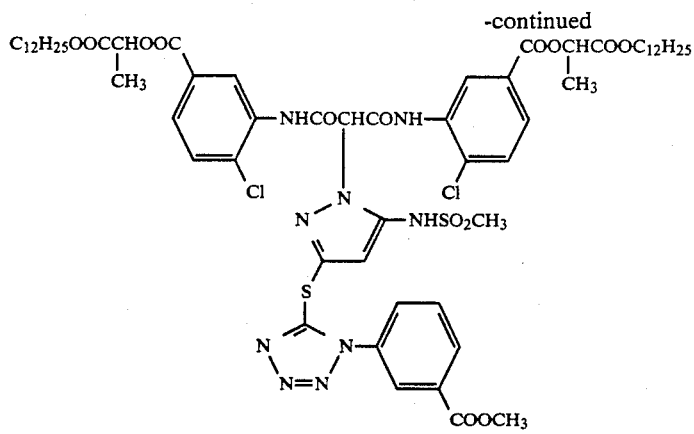
(6)
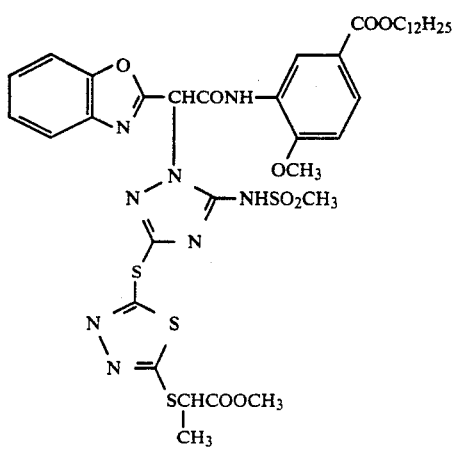
(7)
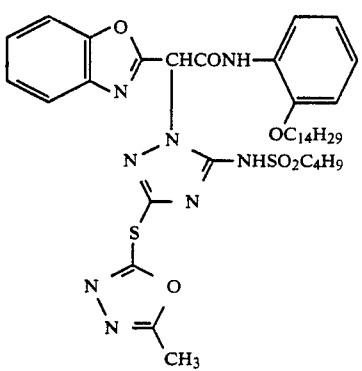
(8)
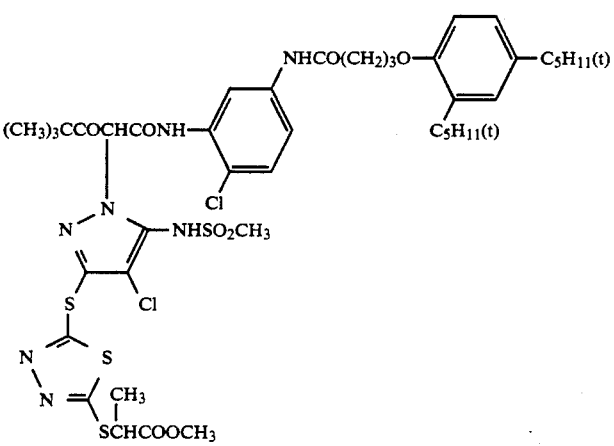
(9)

-continued
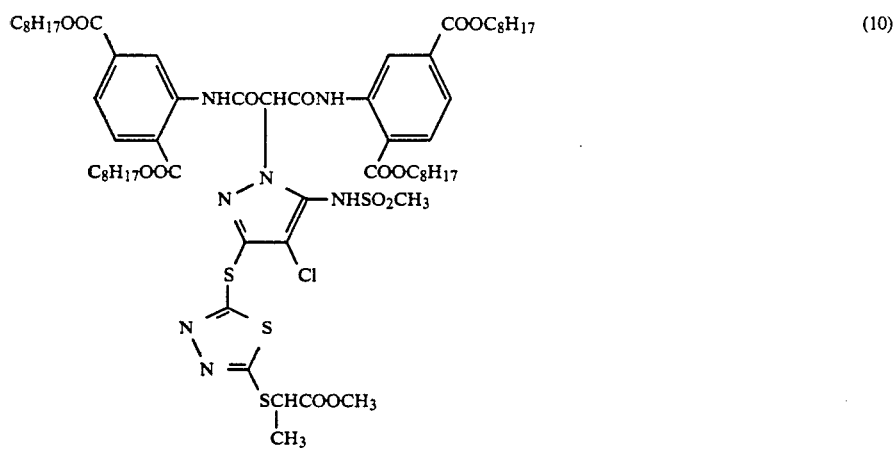
(10)
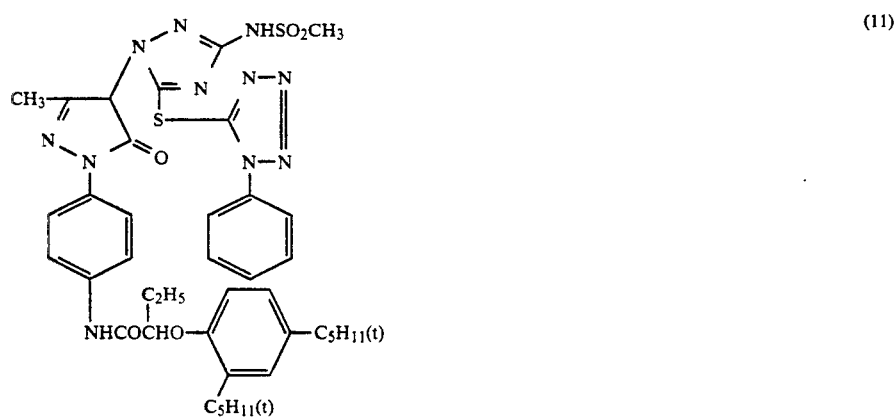
(11)
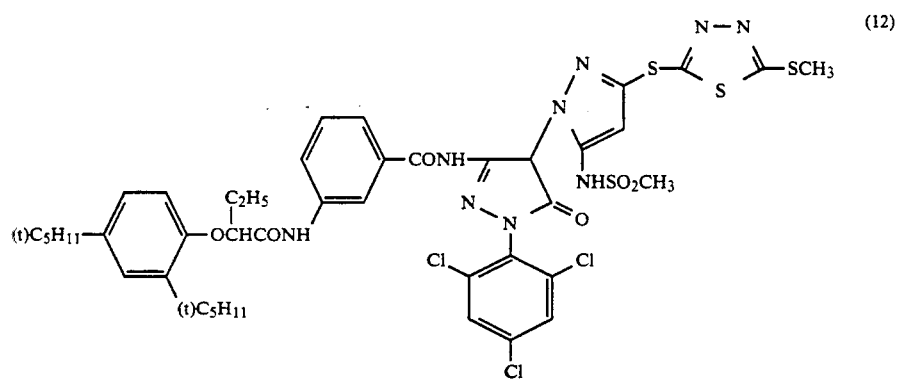
(12)
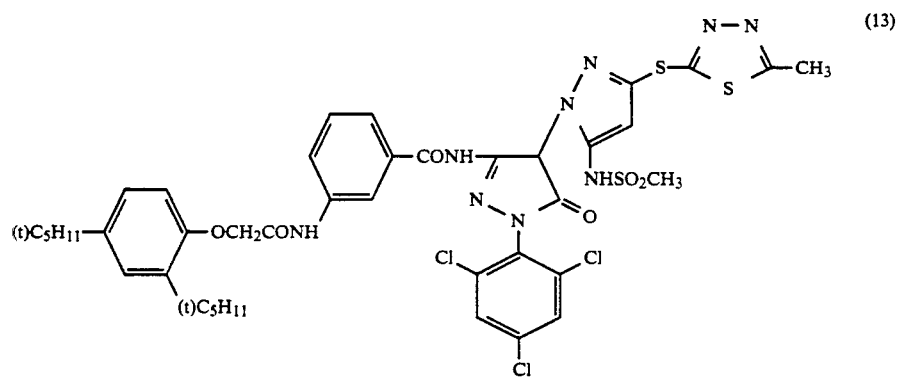
(13)

(14)
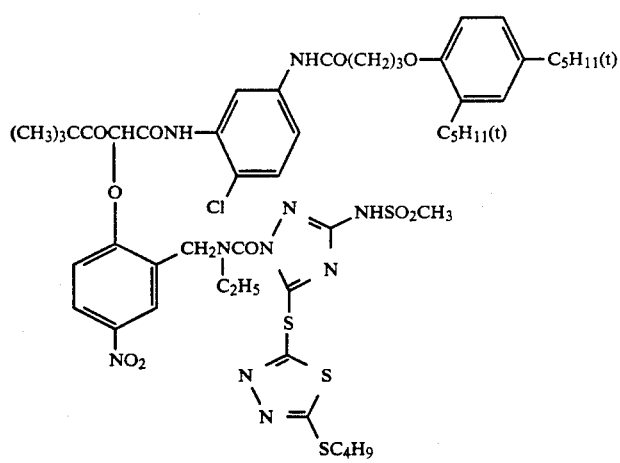
(15)
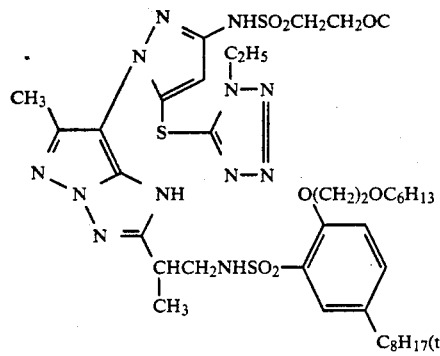
(16)
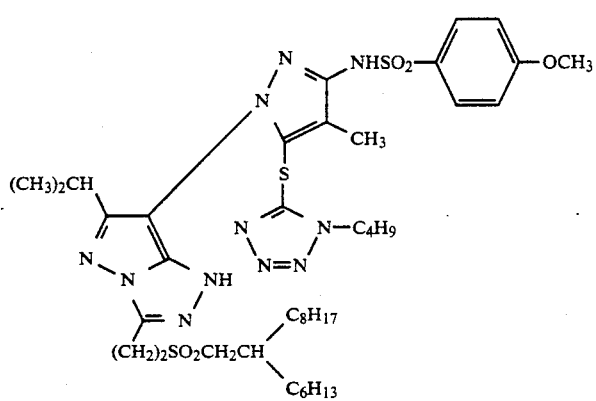
(17)
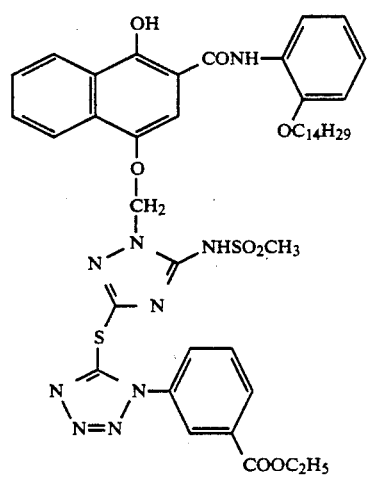

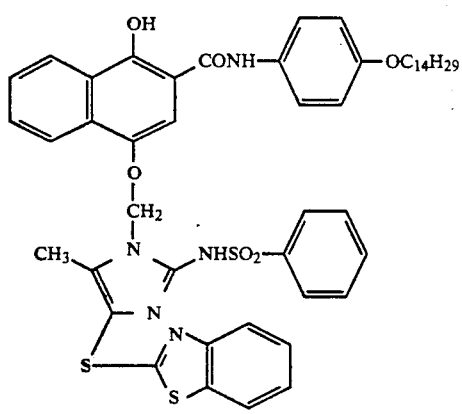
(18)
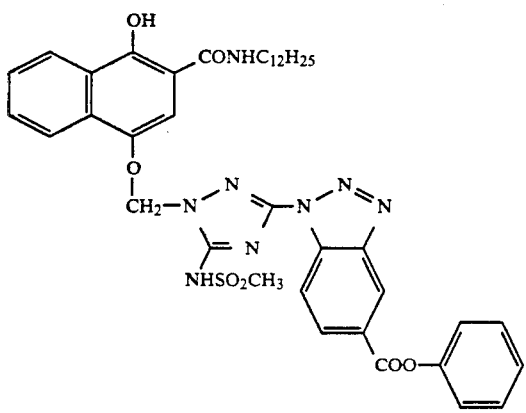
(19)
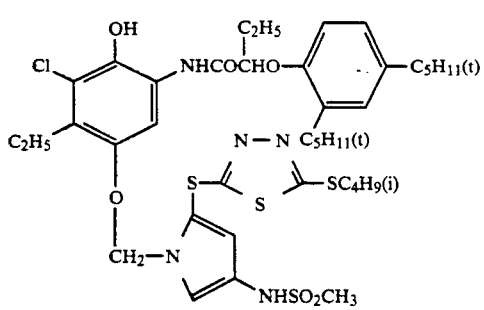
(20)
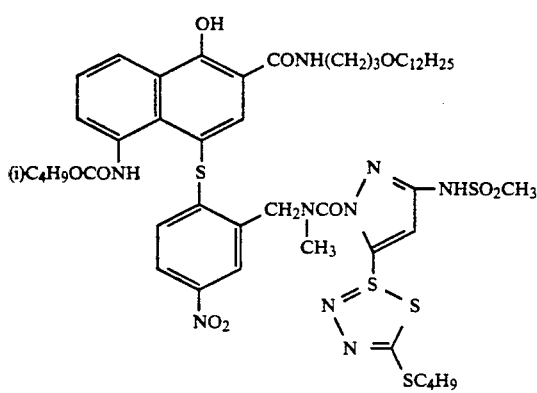
(21)

-continued
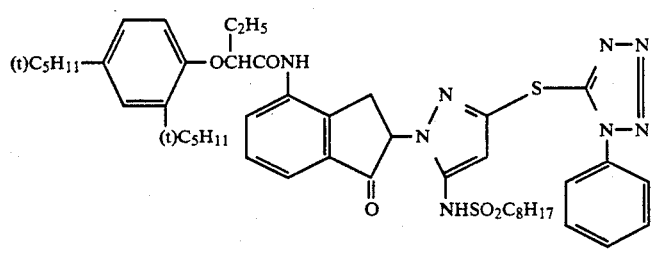 (22)
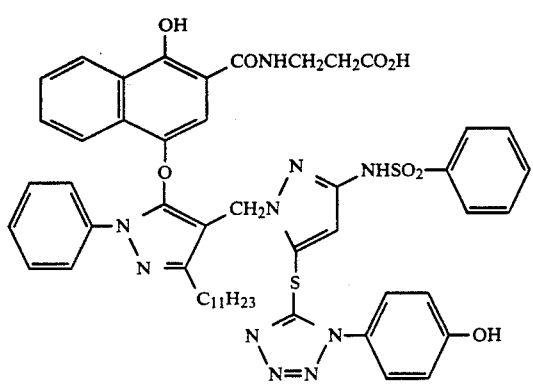 (23)
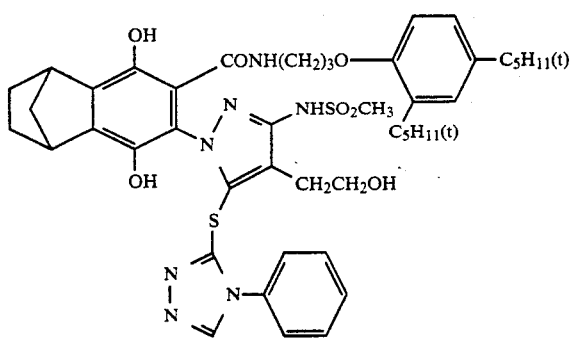 (24)
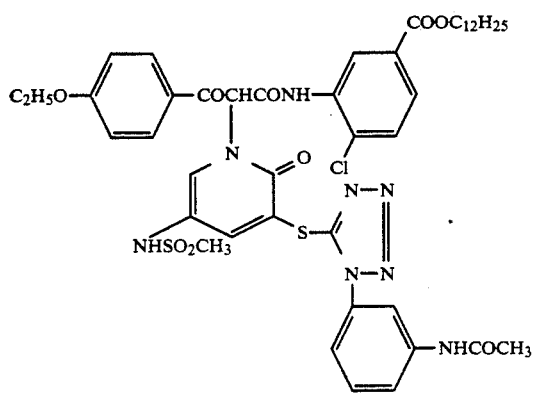 (25)

-continued

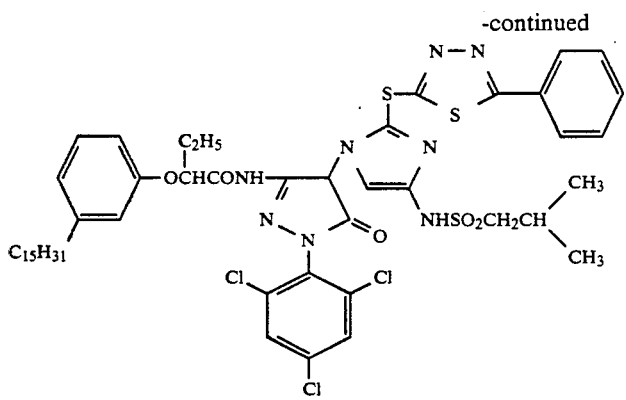
(26)

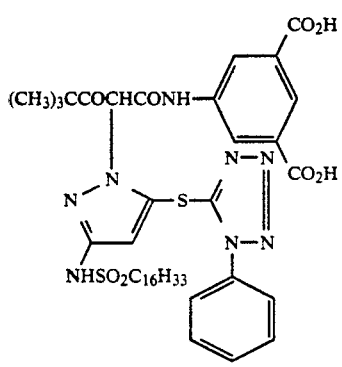
(27)

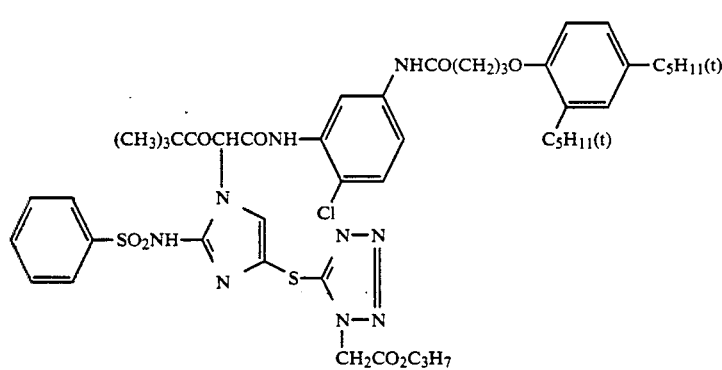
(28)

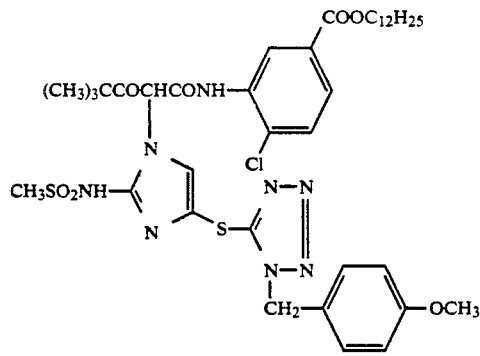
(29)

The compounds according to the present invention can be synthesized using known methods, specifically the same methods as those for synthesis of hetero ring releasing type couplers For instance, they can be synthesized according to the methods as described, for example, in U.S. Pat. Nos. 4,146,369, 4,241,168, 4,076,533, 4,008,086, 4,046,575, 4,229,577, 4,326,024, 4,310,619 and 4,301,235, EP-A-87388, and British Patent 2,132,783A.

Typical synthesis examples of the compounds according to the present invention are illustrated below, and other compounds can be synthesized in a similar manner. Unless otherwise indicated, all parts, percent, ratios and the like are by weight.

SYNTHESIS EXAMPLE 1

Synthesis of Compound (1)

Compound (1) was synthesized according to the route schematically shown below.

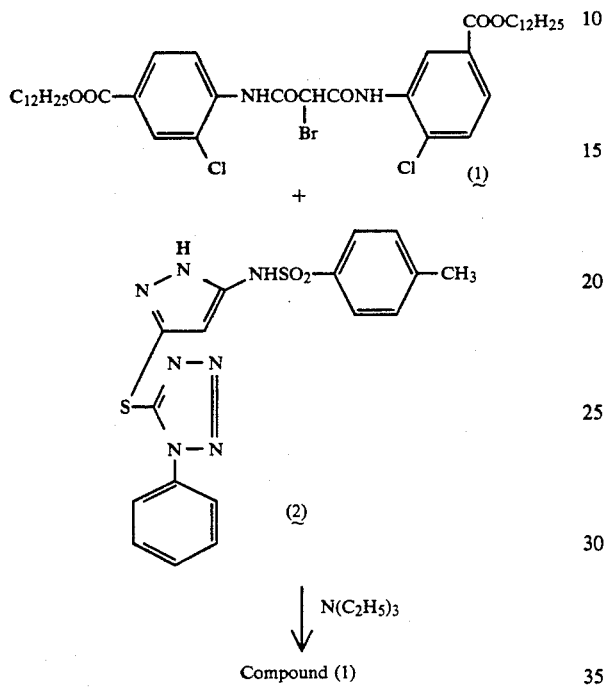

A mixture of 20 g of (1), 21 g of (2), 5 g of triethylamine and 300 ml of N,N-dimethylformamide was stirred for 3 hours. The reaction mixture was poured into 800 ml of water, and extracted with 500 ml of ethyl acetate. The oil layer was separated, and the solvent was distilled off under a reduced pressure. To the residue were added 50 ml of isopropanol and 100 ml of hexane, the solid thus-deposited was collected by filtration to obtain 27 g of the desired Compound (1).

SYNTHESIS EXAMPLE 2

Synthesis of Compound (11)

Compound (11) was synthesized according to the route schematically shown below.

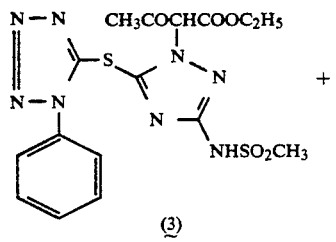

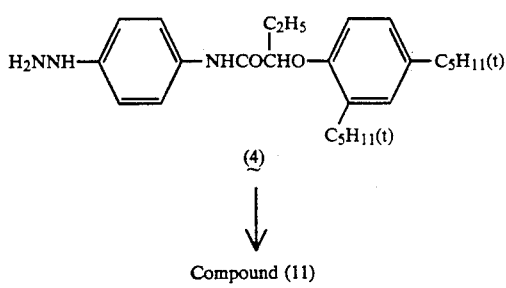

5.7 g of (3) and 4.3 g of (4) were refluxed by heating for 4 hours in a solvent mixture of 30 ml of methoxyethanol and 20 ml of acetic acid. The reaction mixture was poured into water, the solid thus-deposited was collected by filtration and recrystallized from a mixed solvent of acetonitrile and ethyl acetate to obtain 6.8 g of Compound (11).

The color photographic light-sensitive material of the present invention may have at least one blue-sensitive silver halide emulsion layer, at least one green-sensitive silver halide emulsion layer and at least one red-sensitive silver halide emulsion layer on a support. The number of silver halide emulsion layers and light-insensitive layers and the order thereof are not particularly restricted. One typical example is a silver halide photographic material comprising a support having thereon at least one light-sensitive layer group composed of a plurality of silver halide emulsion layers which have substantially the same spectral sensitivity but different speeds. The light-sensitive layer group is a unit light-sensitive layer having a spectral sensitivity to any of blue light, green light and red light. In a multilayer silver halide color photographic material, the unit light-sensitive layers are generally provided in the order of a red-sensitive layer, a green-sensitive layer and a blue-sensitive layer from the support. The order of these layers can be varied depending on the purpose. Further, a layer structure wherein a light-sensitive layer having a different spectral sensitivity is sandwiched between two layers having the same spectral sensitivity, may be used.

Various light-insensitive layers such as an intermediate layer can be provided between the above described silver halide light-sensitive layers or as the uppermost layer or the undermost layer.

Couplers and DIR compounds as described, for example, in JP-A-61-43748, JP-A-59-113438, JP-A-59-113440, JP-A-61-20037 and JP-A-61-20038 may be incorporated into such a intermediate layer. Further, the intermediate layer may contain color stain preventing agents conventionally employed.

The plurality of silver halide emulsion layers which form the unit light-sensitive layer preferably have two layer construction comprising a high speed emulsion layer and a low speed emulsion layer as described, for example, in West German Patent 1,121,470 and British Patent 923,045. It is preferred that these layers be disposed in order of increasing speed from the support side. Further, a light-insensitive layer may be provided between the silver halide emulsion layers. Moreover, a low speed emulsion layer may be provided further from the support and a high speed emulsion layer may be provided closest to the support as described, for example, in JP-A-57-112751, JP-A-62-200350, JP-A-62-206541 and JP-A-62-206543.

Specific examples of layer constructions include an order of a low speed blue-sensitive layer (BL)/a high speed blue-sensitive layer (BH)/a high speed green-sensitive layer (GH)/a low speed green-sensitive layer (GL)/a high speed red-sensitive layer (RH)/a low speed red-sensitive layer (RL) from the outer layer to the support, an order of BH/BL/GL/ GH/RH/RL, or an order of BH/BL/GH/GL/RL/RH.

Further, an order of a blue-sensitive layer/GH/RH/GL/RL from the outer layer to the support as described in JP-B-55-34932 (the term "JP-B" as used herein means an "examined Japanese patent publication") may be employed. Moreover, an order of a blue-sensitive layer/GL/RL/GH/RH from the outer layer to the support as described in JP-A-56-25738 and JP-A-62-63936 may also employed.

Furthermore, a layer construction of three layers having different speeds comprising an upper silver halide emulsion layer having the highest speed, an intermediate silver halide emulsion layer having a lower speed than that of the upper layer, and an under silver halide emulsion layer having a lower speed than that of the intermediate layer in order of increasing speed from the support as described in JP-B-49-15495 can be also employed. Where the unit light-sensitive layer of the same spectral sensitivity is composed of three layers having different speeds, an order of an intermediate speed emulsion layer/a high speed emulsion layer/a low speed emulsion layer from the outer layer to the support may be employed as described in JP-A-59-202464.

As described above, various layer constructions and dispositions may be appropriately selected depending on the purpose of the photographic light-sensitive material.

Preferred silver halides are silver iodobromide, silver iodochloride or silver iodochlorobromide each containing about 30 mol % or less of silver iodide, in the photographic emulsion layers of the photographic light-sensitive material used in the present invention. Silver iodobromide or silver iodochlorobromide each containing from about 2 mol % to about 25 mol % of silver iodide is particularly preferred.

The silver halide grains in the silver halide emulsion may have a regular crystal structure, for example, a cubic, octahedral or tetradecahedral structure, an irregular crystal structure, for example, a spherical or tabular structure, a crystal defect, for example, a twin plane, or a composite structure thereof.

The particle size of the silver halide may be varied and include fine grains having a diameter of about 0.2 micron or less to large size grains having a diameter of about 10 microns as a projected area. Further, a polydisperse emulsion and a monodisperse emulsion may be used.

The silver halide photographic emulsion used in the present invention can be prepared using known methods, for example, those as described in *Research Disclosure*, No. 17643 (December, 1978), pages 22 to 23, "I. Emulsion Preparation and Types" and ibid., No. 18716 (November, 1979), page 648, P. Glafkides, *Chimie et Physique Photographique*, Paul Montel (1967), G. F. Duffin, *Photographic Emulsion Chemistry*, The Focal Press (1966), and V. L. Zelikman et al., *Making and Coating Photographic Emulsion*, The Focal Press (1964).

Monodisperse emulsions as described, for example, in U.S. Pat. Nos. 3,574,628 and 3,655,394, and British Patent 1,413,748 are preferably used in the present invention.

Further, tabular silver halide grains having an aspect ratio of about 5 or more can be employed in the present invention. The tabular grains may be easily prepared by the method as described, for example, in Gutoff, *Photographic Science and Engineering*, Vol. 14, pages 248 to 257 (1970), U.S. Pat. Nos. 4,434,226, 4,414,310, 4,433,048 and 4,439,520, and British Patent 2,112,157.

The crystal structure of the silver halide grains may be uniform, composed of different halide compositions between the inner portion and the outer portion, or may have a stratified structure.

Further, silver halide emulsions in which silver halide grains having different compositions are connected upon epitaxial junctions or silver halide emulsions in which silver halide grains are connected with compounds other than silver halide, such as silver thiocyanate, or lead oxide, may also be employed.

Moreover, a mixture of grains having a different crystal structure may be used.

The silver halide emulsions used in the present invention are usually subjected to physical ripening, chemical ripening and spectral sensitization. Various kinds of additives which can be employed in these steps are described in *Research Disclosure*, No. 17643, (December, 1978) and ibid., No. 18716 (November, 1979) and relevant items thereof are summarized in the table shown below.

Further, known photographic additives which can be used in the present invention are also described in the above mentioned literature and relevant items thereof are summarized in the table below.

| | Kind of Additives | RD 17643 | RD 18716 |
|---|---|---|---|
| 1. | Chemical Sensitizers | Page 23 | Page 648, right column |
| 2. | Sensitivity Increasing Agents | | Page 648, right column |
| 3. | Spectral Sensitizers and Supersensitizers | Pages 23 to 24 | Page 648, right column to page 649, right column |
| 4. | Whitening Agents | Page 24 | |
| 5. | Antifoggants and Stabilizers | Pages 24 to 25 | Page 649, right column |
| 6. | Light-Absorbers, Filter Dyes and Ultra-violet Ray Absorbers | Pages 25 to 26 | Page 649, right column to page 650, left column |
| 7. | Antistaining Agents | Page 25, right column | Page 650, left column to right column |
| 8. | Dye Image Stabilizers | Page 25 | |
| 9. | Hardeners | Page 26 | Page 651, left column |
| 10. | Binders | Page 26 | Page 651, left column |
| 11. | Plasticizers and Lubricants | Page 27 | Page 650, right column |
| 12. | Coating Aids and Surfactants | Pages 26 to 27 | Page 650, right column |
| 13. | Antistatic Agents | Page 27 | Page 650, right column |

Further, in order to prevent degradation of photographic properties due to formaldehyde gas, it is preferred to add a compound capable of reacting with formaldehyde to fix it as described in U.S. Pat. Nos. 4,411,987 and 4,435,503 to the photographic light-sensitive material.

Various color couplers can be employed in the present invention and specific examples thereof are described in the patents cited in *Research Disclosure*, No. 17643, "VII-C" to "VII-G".

Suitable yellow couplers which can be used in the present invention, for example, include those as described in U.S. Pat. Nos. 3,933,501, 4,022,620, 4,326,024, 4,401,752 and 4,248,961, JP-B-58-10739, British Patents 1,425,020 and 1,476,760, U.S. Pat. Nos. 3,973,968, 4,314,023 and 4,511,649, and EP-A-249473 which are preferred.

Suitable magenta couplers which can be used in the present invention are 5-pyrazolone type and pyrazoloazole type compounds which are preferred. Magenta couplers as described, for example, in U.S. Pat. Nos. 4,310,619 and 4,351,897, European Patent 73,636, U.S Pat. Nos. 3,061,432 and 3,725,067, Research Disclosure, No. 24220 (June, 1984), JP-A-60-33552, Research Disclosure, No. 24230 (June, 1984), JP-A-60-43659, JP-A-61-72238, JP-A-60-35730, JP-A-55-118034, JP-A-60-18951, and U.S. Pat. Nos. 4,500,630, 4,540,654 and 4,556,630, and WO(PCT) 88/04795 are particularly preferred.

Suitable cyan couplers which can be used in the present invention include phenol type and naphthol type couplers. Cyan couplers as described, for example, in U.S. Pat. Nos. 4,052,212, 4,146,396, 4,228,233, 4,296,200, 2,369,929, 2,801,171, 2,772,162, 2,895,826, 3,772,002, 3,758,308, 4,334,011 and 4,327,173, West German Patent Application (OLS) No. 3,329,729, EP-A-121365 and EP-A-249453, U.S. Pat. Nos. 3,446,622, 4,333,999, 4,753,871, 4,451,559, 4,427,767, 4,690,889, 4,254,212 and 4,296,199, and JP-A-61-42658 which are preferred.

Examples of colored couplers for correcting undesirable absorptions of dyes formed include those as described, for example, in Research Disclosure, No. 17643, "VII-G", U.S. Pat. No. 4,163,670, JP-B-57-39413, U.S. Pat. Nos. 4,004,929 and 4,138,258, and British Patent 1,146,368 are preferably employed.

Couplers capable of forming appropriately diffusible dyes are those as described, for example, in U.S. Pat. No. 4,366,237, British Patent 2,125,570, European Patent 96,570, and West German Patent Application (OLS) No. 3,234,533 and are preferable.

Typical examples of polymerized dye forming couplers are described, for example, in U.S. Pat. Nos. 3,451,820, 4,080,211, 4,367,282, 4,409,320 and 4,576,910, and British Patent 2,102,173.

Couplers capable of releasing a photographically useful moiety during the course of coupling can be also employed with advantage in the present invention. As DIR couplers capable of releasing a development inhibitor, those as described, for example, in the patents cited in Research Disclosure, No. 17643, "VII-F" described above, JP-A-57-151944, JP-A-57-154234, JP-A-60-184248, JP-A-63-37346, and U.S. Pat. No. 4,248,962 are preferred.

Suitable couplers which release imagewise a nucleating agent or a development accelerator at the time of development are those as described, for example, in British Patents 2,097,140 and 2,131,188, JP-A-59-157638, and JP-A-59-170840 and they are preferred.

Furthermore, competing couplers such as those described, for example, in U.S. Pat. No. 4,130,427; polyequivalent couplers such as those described, for example, in U.S. Pat. Nos. 4,283,472, 4,338,393 and 4,310,618; DIR redox compound or DIR coupler releasing couplers or DIR coupler or DIR redox compound releasing redox compound such as those described, for example, in JP-A-60-185950 and JP-A-62-24252; couplers capable of releasing a dye which turns to a colored form after being released such as those described, for example, in EP-A-173302; bleach accelerator releasing couplers such as those described, for example, in Research Disclosure, No. 11449, ibid, No. 24241 and JP-A-61-201247; ligand releasing couplers such as those described, for example, in U.S. Pat. No. 4,553,477; and couplers capable of releasing a leuco dye such as those described, for example, in JP-A-63-75747 may be employed in the photographic light-sensitive material of the present invention.

The couplers which can be used in the present invention can be introduced into the photographic light-sensitive material using various known dispersing methods.

Suitable examples of organic solvents having a high boiling point which can be employed in an oil droplet-in-water type dispersing method are described, for example, in U.S. Pat. No. 2,322,027.

Specific examples of organic solvents having a high boiling point of not less than 175° C. at normal pressure and can be employed in the oil droplet-in-water type dispersing method include phthalic acid esters (for example, dibutyl phthalate, dicyclohexyl phthalate, di-2-ethylhexyl phthalate, decyl phthalate, bis(2,4-di-tert-amylphenyl)phthalate, bis(2,4-di-tert-amylphenyl)-isophthalate, or bis(1,1-diethylpropyl)phthalate, phosphonic acid or phosphonic acid esters (for example, triphenyl phosphate, tricresyl phosphate, 2-ethylhexyl diphenyl phosphate, tricyclohexyl phosphate, tri-2-ethylhexyl phosphate, tridodecyl phosphate, tributoxyethyl phosphate, trichloropropyl phosphate, or di-2-ethylhexyl phenylphosphonate), benzoic acid esters (for example, 2-ethylhexyl benzoate, dodecyl benzoate, or 2-ethylhexyl-p-hydroxybenzoate), amides (for example, N,N-diethyldodecanamide, N,N-diethyllaurylamide, or N-tetradecylpyrrolidone), alcohols or phenols (for example, isostearyl alcohol, or 2,4-di-tert-amylphenol), aliphatic carboxylic acid esters (for example, bis(2-ethylhexyl)sebacate, dioctyl azelate, gycerol tributyrate, isostearyl lactate, or trioctyl citrate), aniline derivatives (for example, N,N-dibutyl-2-butoxy-5-tert-octylaniline), and hydrocarbons (for example, paraffin, dodecylbenzene, or diisopropylnaphthalene).

Further, an organic solvent having a boiling point at least about 30° C. and preferably having a boiling point above 50° C. but below about 160° C. can be used as an auxiliary solvent. Typical examples of auxiliary solvents include ethyl acetate, butyl acetate, ethyl propionate, methyl ethyl ketone, cyclohexanone, 2-ethoxyethyl acetate, or dimethylformamide.

The processes and effects of latex dispersing methods and the specific examples of latexes for loading are described, for example, in U.S. Pat. No. 4,199,363, West German Patent Application (OLS) Nos. 2,541,274 and 2,541,230.

The present invention can be applied to various color photographic light-sensitive materials, and typical examples thereof include color negative films for general use or cinematography, color reversal films for slides or television, color papers, color positive films, and color reversal papers.

Suitable supports which can be used in the present invention are described, for example, in Research Disclosure, No. 17643, page 28 and ibid., No. 18716, page 647, right column to page 648, left column, as mentioned above.

It is preferred that the total layer thickness of all hydrophilic colloid layers on the emulsion layer side of the photographic light-sensitive material according to the present invention is not more than 28 μm and a layer swelling rate of T½ is not more than 30 seconds. The layer thickness means the thickness of layer measured after preservation under the conditions of 25° C. and relative humidity of 55% for 2 days. The layer swelling rate of T½ is determined according to known methods in the field of the art. For instance, the degree of swelling can be measured using a swellometer of the type described in A. Green, *Photogr. Sci. Eng.*, Vol. 19, No. 2, page 124 to 129, and T½ is defined as a time necessary for reaching a layer thickness to a half of a saturated layer thickness which is 90% of the maximum swelling layer thickness obtained when treated in a color developing solution at 30° C. for 3 minutes and 15 seconds.

The layer swelling rate of T½ can be controlled by adding a hardening agent to a gelatin binder or changing the aging condition after coating.

The swelling factor is preferably from 150% to 400%. The swelling factor can be calculated by the formula of (maximum swelling layer thickness − layer thickness)/layer thickness wherein the maximum swelling layer thickness has the same meaning as defined above.

The color photographic light-sensitive material according to the present invention can be subjected to development processing in a conventional manner as described in *Research Disclosure*, No. 17643, pages 28 to 29 and ibid., No. 18716, page 651, left column to right column, as mentioned above.

The color developing solution which can be used in the development processing of the color photographic light-sensitive material according to the present invention is an alkaline aqueous solution containing preferably an aromatic primary amine type color developing agent as a main component. As the color developing agent, while an aminophenol type compound is useful, a p-phenylenediamine type compound is preferably employed. Typical examples of p-phenylenediamine type compounds include 3-methyl-4-amino-N,N-diethylaniline, 3-methyl-4-amino-N-ethyl-N-β-hydroxyethylaniline, 3-methyl-4-amino-N-ethyl-N-β-methanesulfonamidoethylaniline, 3-methyl-4-amino-N-ethyl-β-methoxyethylaniline, or sulfate, hydrochloride or p-toluenesulfonate thereof.

Two or more kinds of color developing agents may be employed in combination, depending on the purpose.

The color developing solution ordinarily contains pH buffering agents, such as carbonates, borates or phosphates of alkali metals; and development inhibitors or anti-fogging agents such as bromides, iodides, benzimidazoles, benzothiazoles, or mercapto compounds. Further, if necessary, the color developing solution may contain various preservatives such as hydroxylamine, diethylhydroxylamine, sulfites, hydrazines, phenylsemicarbazides, triethanolamine, catechol sulfonic acids, or triethylenediamine(1,4-diazabicyclo[2,2,2]octane); organic solvents such as ethyleneglycol, or diethylene glycol; development accelerators such as benzyl alcohol, polyethylene glycol, quarternary ammonium salts, or amines; dye forming couplers; competing couplers; fogging agents such as sodium borohydride; auxiliary developing agents such as 1-phenyl-3-pyrazolidone; viscosity imparting agents; and various chelating agents such as aminopolycarboxylic acids, aminopolyphosphonic acids, alkylphosphonic acids, or phosphonocarboxylic acids. Representative examples of suitable chelating agents include ethylenediaminetetraacetic acid, nitrilotriacetic acid, diethylenetriaminepentaacetic acid, cyclohexanediaminetetraacetic acid, hydroxyethyliminodiacetic acid, 1-hydroxyethylidene-1,1-diphosphonic acid, nitrilo-N,N,N-trimethylenephosphonic acid, ethylenediamine-N,N,N,N-tetramethylenephosphonic acid, ethylenediamine-di(o-hydroxyphenylacetic acid), and salts thereof.

In conducting reversal processing, color development is usually conducted after black-and-white development. In a black-and-white developing solution, known black-and-white developing agents, for example, dihydroxybenzenes such as hydroquinone, 3-pyrazolidones such as 1-pheyl-3-pyrazolidone, or aminophenols such as N-methyl-p-aminophenol may be employed individually or in combination.

The pH of the color developing solution or the black-and-white developing solution is usually a pH of from 9 to 12. Further, the amount of replenishment for the developing solution can be varied depending on the color photographic light-sensitive materials to be processed, but is generally not more than 3 liters per square meter of the photographic light-sensitive material. The amount of replenishment can be reduced to not more than 500 ml by decreasing the bromide ion concentration in the replenisher. In reducing the amount of replenishment, it is preferred to prevent evaporation and aerial oxidation of the processing solution by reducing the area of a processing tank which is contact with the air. Further, the amount of replenishment can be reduced using a means which restrains accumulation of bromide ion in the developing solution.

The processing time for color development is usually in the range from 2 minutes to 5 minutes. However, it is possible to reduce the processing time by performing the color development at high temperature and high pH using a high concentration of color developing agent.

After color development, the photographic emulsion layers are usually subjected to a bleach processing. The bleach processing can be performed simultaneously with a fix processing (bleach-fix processing), or it can be performed independently from the fix processing. Further, for the purpose of a rapid processing, a processing method wherein, after a bleach processing, a bleach-fix processing is conducted may be employed. Moreover, depending on the purpose, a continuous two tank bleach-fixing bath can be used, fix processing before bleach-fix processing can be conducted, or bleach processing after bleach-fix processing can be conducted.

Examples of suitable bleaching agents which can be employed in the bleach processing or bleach-fix processing include compounds of a multivalent metal such as iron(III), cobalt(III), chromium(IV), or copper(II); peracids; quinones; or nitro compounds. Representative examples of bleaching agents include ferricyanides; dichloromates; organic complex salts of iron(III) or cobalt(III), for example, complex salts of aminopolycarboxylic acids (such as ethylenediaminetetraacetic acid, diethylenetriaminepentaacetic acid, cyclohexanediaminetetraacetic acid, methyliminodiacetic acid, 1,3-diaminopropanetetraacetic acid, or glycol ether diaminetetraacetic acid), or complex salts of organic acids (such as citric acid, tartaric acid, or malic acid); persulfates; bromates; permanganates; or nitrobenzenes. Of these compounds, iron(III) complex salts of aminopolycarboxylic acids represented by iron(III) complex salt of ethylenediaminetetraacetic acid and persulfates are preferred in view of rapid processing and less environmental pollution. Furthermore, iron(III) complex salts of aminopolycarboxylic acids are particularly useful in both bleaching solutions and bleach-fixing solutions.

The pH of the bleaching solution or bleach-fixing solution containing an iron(III) complex salt of aminopolycarboxylic acid is usually in a range from 5.5 to 8. For the purpose of rapid processing, it is possible to process at a pH lower than the above described range.

A bleach accelerating agent can be used, if desired in the bleaching solution, the bleach-fixing solution or a prebath thereof. Specific examples of suitable bleach accelerating agents include compounds having a mercapto group or a disulfide bond as described, for example, in U.S. Pat. No. 3,893,858, West German Patents 1,290,812 and 2,059,988, JP-A-53-32736, JP-A-53-57831, JP-A-53-37418, JP-A-53-72623, JP-A-53-95630, JP-A-53-95631, JP-A-53-104232, JP-A-53-124424, JP-A-53-141623, JP-A-53-28426, and Research Disclosure, No. 17129 (July 1978); thiazolidine derivatives as described, for example, in JP-A-50-140129; thiourea derivatives as described, for example, in JP-B-45-8506, JP-A-52-20832, JP-A-53-32735 and U.S. Pat. No. 3,706,561; iodides as described, for example, in West German Patent 1,127,715 and JP-A-58-16235; polyoxyethylene compounds as described, for example, in West German Patents 966,410 and 2,748,430; polyamine compounds as described, for example, in JP-B-45-8836; compounds as described, for example, in JP-A-49-42434, JP-A-49-59644, JP-A-53-94927, JP-A-54-35727, JP-A-55-26506, and JP-A-58-163940; and bromide ions. Of these compounds, compounds having a mercapto group or a disulfide bond are preferred in view of their large bleach accelerating effects. Particularly, the compounds as described in U.S. Pat. No. 3,893,858, West German Patent 1,290,812 and JP-A-53-95630 are preferred. Further, the compounds as described in U.S. Pat. No. 4,552,834 are also preferred. These bleach accelerating agents may be incorporated into the color photographic light-sensitive material. These bleach accelerating agents are particularly effectively employed when color photographic light sensitive materials for photographing are subjected to bleach-fix processing.

Suitable fixing agents which can be employed in the fixing solution or bleach-fixing solution include thiosulfates, thiocyanate, thioether compounds, thioureas, or a large amount of iodide. Of these compounds, thiosulfates are generally employed. Particularly, ammonium thiosulfate is most widely employed. It is preferred to use sulfites, bisulfites or carbonylbisulfite adducts as preservatives in the bleach-fixing solution.

After a desilvering step, the silver halide color photographic material according to the present invention is generally subjected to a water washing step and/or a stabilizing step.

The amount of water required for the water washing step may vary widely depending on the characteristics of photographic light-sensitive materials (the elements used therein, for example, couplers, etc.), the uses thereof, the temperature of washing water, the number of water washing tanks (stages), the replenishment system such as countercurrent or concurrent, or other various conditions. The relationship between a number of water washing tanks and an amount of water in a multi-stage countercurrent system can be determined based on the method as described in *Journal of the Society of Mothion Picture and Television Engineers*, Vol. 64, pages 248 to 253 (May, 1955).

According to the multi-stage countercurrent system described in the above literature, the amount of water for washing can be significantly reduced. However, increases in the residence of water in a tank cause a propagation of bacteria and problems such as adhesion of floatage formed on the photographic materials occur. In the method of processing the silver halide color photographic material according to the present invention, a method for reducing amounts of calcium ions and magnesium ions as described in JP-A-62-288838 can be particularly effectively employed in order to solve such problems. Further, sterilizers, for example, isothiazolone compounds as described in JP-A-57-8542, thiabendazoles, chlorine type sterilizers such as sodium chloroisocyanurate, benzotriazoles, sterilizers as described in Hiroshi Horiguchi, *Bokin-Bobai No Kagaku, Biseibutsu No Mekkin-, Sakkin-, Bobai-Gijutsu*, edited by Eiseigijutsu Kai, and *Bokin-Bobaizai Jiten*, edited by Nippon Bokin-Bobai Gakkai can be employed.

The pH of the washing water used in the processing of the photographic light-sensitive materials according to the present invention is usually from 4 to 9, preferably from 5 to 8. The temperature of the washing water and the time for the water washing step can be varied depending on the characteristics of or the uses of the photographic light-sensitive materials. However, it is generally in the range of from 15° C. to 45° C. and a period from 20 sec. to 10 min. and preferably a range of from 25° C. to 40° C. and a period from 30 sec. to 5 min.

The photographic light-sensitive material of the present invention can also be directly processed with a stabilizing solution in place of the above-described water washing step. Any of known methods as described, for example, in JP-A-57-8543, JP-A-58-14834 and JP-A-60-220345 can be employed for such a stabilizing process.

Further, it is possible to conduct the stabilizing process subsequent to the above-described water washing process. One example thereof is a stabilizing bath containing formaldehyde and a surface active agent, which is employed as a final bath in the processing of color photographic light-sensitive materials for photographing. Various chelating agents and antimolds may also be added to such a stabilizing bath.

Overflow solutions resulting from replenishment of the above-described washing water and/or stabilizing solution may be reused in other steps such as a desilvering step.

To simplify and accelerate the processing, a color developing agent may be incorporated into the silver halide color photographic material according to the present invention. In order to incorporate the color developing agent, it is preferred to employ various precursors of color developing agents. Suitable examples of the precursors of developing agents include indoaniline type compounds as described in U.S. Pat. Nos. 3,342,597, Schiff's base type compounds as described in U S. Pat. No. 3,342,599 and *Research Disclosure*, No. 14850 and ibid., No. 15159, aldol compounds as described in *Research Disclosure*, No. 13924, metal salt complexes as described in U.S. Pat. No. 3,719,492, and urethane type compounds as described in JP-A-53-135628.

Further, the silver halide color photographic material according to the present invention may contain, if desired, various 1-phenyl-3-pyrazolidones for the purpose of accelerating color development. Typical examples of these compounds include those as described, for example in JP-A-56-64339, JP-A-57-144547, and JP-A-58-115438.

In the present invention, various kinds of processing solutions can be employed at a temperature range from 10° C. to 50° C. Although the standard temperature is from 33° C. to 38° C., it is possible to carry out the processing at higher temperatures in order to accelerate the processing whereby the processing time is shortened, or at lower temperatures in order to achieve improvements in image quality and to maintain stability of the processing solutions.

Further, for the purpose of reducing an amount of silver employed in the color photographic light-sensitive material, the photographic processing may be conducted utilizing color intensification employing cobalt or hydrogen peroxide as described in West German Patent 2,226,770 or U.S. Pat. No. 3,674,499.

Moreover, the silver halide color photographic material of the present invention can be applied to heat-developable light-sensitive materials as described, for example, in U.S. Pat. No. 4,500,626, JP-A-60-133449, JP-A-59-218443, JP-A-61-238056 and EP-A-210660.

The present invention is explained in greater detail with reference to the following example, but the present invention should not be construed as being limited thereto.

EXAMPLE 1

On a cellulose triacetate film support provided with a subbing layer was coated each layer having the composition set forth below to prepare a multilayer color photographic light-sensitive material which was designated Sample 101.

In the compositions of the layers, the coating amounts of silver halide and colloidal silver are shown as g/m² units in terms of silver, while the coating amounts of the couplers, additives and gelatin are shown as g/m² units, and the coating amounts of the sensitizing dyes are shown as mol number per mol of silver halide present in the same layer.

The symbols which denote additives used below have the meanings described in the following. When the additive has two or more functions, one of them is indicated as representative.

UV: Ultraviolet light absorbing agent
Solv: Organic solvent having a high boiling point
ExF: Dye
ExS: Sensitizing dye
ExC: Cyan coupler
ExM: Magenta coupler
ExY: Yellow coupler
Cpd: Additive

| First Layer: Antihalation Layer | |
|---|---|
| Black colloidal silver | 0.15 |
| Gelatin | 2.9 |
| UV-1 | 0.03 |
| UV-2 | 0.06 |
| UV-3 | 0.07 |
| Solv-2 | 0.08 |
| ExF-1 | 0.01 |
| ExF-2 | 0.01 |
| Second Layer: Low-Speed Red-Sensitive Emulsion Layer | |
| Silver Iodobromide Emulsion (AgI: 4 mol %, uniform AgI type, diameter corresponding to sphere: 0.4 μm, coefficient of variation of diameter corresponding to sphere: 37%, tabular grain, diameter/thickness ratio: 3.0) | 0.4 (as silver) |
| Gelatin | 0.8 |
| ExS-1 | $2.3 \times 10^{-4}$ |
| ExS-2 | $1.4 \times 10^{-4}$ |
| ExS-5 | $2.3 \times 10^{-4}$ |
| ExS-7 | $8.0 \times 10^{-6}$ |
| ExC-1 | 0.17 |
| ExC-2 | 0.03 |
| ExC-3 | 0.13 |
| Third Layer: Medium-Speed Red Sensitive Emulsion Layer | |
| Silver Iodobromide Emulsion (AgI: 6 mol %, internal high AgI type, with core/shell ratio of 2:1, diameter corresponding to sphere: 0.65 μm, coefficient of variation of diameter corresponding to sphere: 25%, tabular grain, diameter/thickness ratio: 2.0) | 0.65 (as silver) |
| Silver Iodobromide Emulsion (AgI: 4 mol %, uniform AgI type, diameter corresponding to sphere: 0.4 μm, coefficient of variation of diameter corresponding to sphere: 37%, tabular grain, diameter/thickness ratio: 3.0) | 0.1 (as silver) |
| Gelatin | 1.0 |
| ExS-1 | $2 \times 10^{-4}$ |
| ExS-2 | $1.2 \times 10^{-4}$ |
| ExS-5 | $2 \times 10^{-4}$ |
| ExS-7 | $7 \times 10^{-6}$ |
| ExC-1 | 0.31 |
| ExC-2 | 0.01 |
| ExC-3 | 0.06 |
| Fourth Layer: High-Speed Red-sensitive Emulsion Layer | |
| Silver Iodobromide Emulsion (AgI: 6 mol %, internal high AgI type, with core/shell ratio of 2:1, diameter corresponding to sphere: 0.7 μm, coefficient of variation of diameter corresponding to sphere: 25%, tabular grain, diameter/thickness ratio: 2.5) | 0.9 (as silver) |
| Gelatin | 0.8 |
| ExS-1 | $1.6 \times 10^{-4}$ |
| ExS-2 | $1.6 \times 10^{-4}$ |
| ExS-5 | $1.6 \times 10^{-4}$ |
| ExS-7 | $6 \times 10^{-4}$ |
| ExC-1 | 0.07 |
| ExC-4 | 0.05 |
| Solv-1 | 0.07 |
| Solv-2 | 0.20 |
| Cpd-7 | $4.6 \times 10^{-4}$ |
| Fifth Layer: Intermediate Layer | |
| Gelatin | 0.6 |
| UV-4 | 0.03 |
| UV-5 | 0.04 |
| Cpd-1 | 0.1 |
| Polyethyl acrylate latex | 0.08 |
| Solv-1 | 0.05 |
| Sixth Layer: Low-Speed Green-Sensitive Emulsion Layer | |
| Silver Iodobromide Emulsion (AgI: 4 mol %, uniform AgI type, diameter corresponding to sphere: 0.4 μm, coefficient of variation of diameter corresponding to sphere: 37%, tabular grain, diameter/thickness ratio: 2.0) | 0.18 (as silver) |
| Gelatin | 0.4 |
| ExS-3 | $2 \times 10^{-4}$ |
| ExS-4 | $7 \times 10^{-4}$ |
| ExS-5 | $1 \times 10^{-4}$ |
| ExM-5 | 0.11 |
| ExM-7 | 0.03 |
| ExY-8 | 0.01 |
| Solv-1 | 0.09 |
| Solv-4 | 0.01 |
| Seventh Layer: Medium-Speed Green-Sensitive Emulsion Layer | |
| Silver Iodobromide Emulsion (AgI: 4 mol %, surface high AgI type, with core/shell ratio of 1:1, diameter corresponding to sphere: 0.5 μm, coefficient of variation of | 0.27 (as silver) |

| | |
|---|---|
| diameter corresponding to sphere: 20%, tabular grain, diameter/thickness ratio: 4.0) | |
| Gelatin | 0.6 |
| ExS-3 | $2 \times 10^{-4}$ |
| ExS-4 | $7 \times 10^{-4}$ |
| ExS-5 | $1 \times 10^{-4}$ |
| ExM-5 | 0.17 |
| ExM-7 | 0.04 |
| ExY-8 | 0.02 |
| Solv-1 | 0.14 |
| Solv-4 | 0.02 |
| Eighth Layer: High-Speed Green-Sensitive Emulsion Layer | |
| Silver Iodobromide Emulsion (AgI: 8.7 mol %, multi-layer structure grain having silver amount ratio of 3:4:2, AgI content: 24 mol, 0 mol, 3 mol from inside, diameter corresponding to sphere: 0.7 μm, coefficient of variation of diameter corresponding to sphere: 25%, tabular grain, diameter/thickness ratio: 1.6) | 0.7 (as silver) |
| Gelatin | 0.8 |
| ExS-4 | $5.2 \times 10^{-4}$ |
| ExS-5 | $1 \times 10^{-4}$ |
| ExS-8 | $0.3 \times 10^{-4}$ |
| ExM-5 | 0.1 |
| ExM-6 | 0.03 |
| ExY-8 | 0.02 |
| ExC-1 | 0.02 |
| ExC-4 | 0.01 |
| Solv-1 | 0.25 |
| Solv-2 | 0.06 |
| Solv-4 | 0.01 |
| Cpd-7 | $1 \times 10^{-4}$ |
| Ninth Layer: Intermediate Layer | |
| Gelatin | 0.6 |
| Cpd-1 | 0.04 |
| Polyethyl acrylate latex | 0.12 |
| Solv-1 | 0.02 |
| Tenth Layer: Donor Layer of Interimage Effect to Red-Sensitive Layer | |
| Silver Iodobromide Emulsion (AgI: 6 mol %, internal high AgI type, with core/shell ratio of 2:1, diameter corresponding to sphere: 0.7 μm, coefficient of variation of diameter corresponding to sphere: 25%, tabular grain, diameter/thickness ratio: 2.0) | 0.68 (as silver) |
| Silver Iodobromide Emulsion (AgI: 4 mol %, uniform AgI type, diameter corresponding to sphere: 0.4 μm, coefficient of variation of diameter corresponding to sphere: 37%, tabular grain, diameter/thickness ratio: 3.0) | 0.19 (as silver) |
| Gelatin | 1.0 |
| ExS-3 | $6 \times 10^{-4}$ |
| ExM-10 | 0.19 |
| Solv-1 | 0.20 |
| Eleventh Layer: Yellow Filter Layer | |
| Yellow Colloidal Silver | 0.06 |
| Gelatin | 0.8 |
| Cpd-2 | 0.13 |
| Solv-1 | 0.13 |
| Cpd-1 | 0.07 |
| Cpd-6 | 0.002 |
| H-1 | 0.13 |
| Twelfth Layer: Low-Speed Blue-sensitive Emulsion Layer | |
| Silver Iodobromide Emulsion (AgI: 4.5 mol %, uniform AgI type, diameter corresponding to sphere: 0.7 μm, coefficient of variation of diameter corresponding to sphere: 15%, tabular grain, diameter/thickness ratio: 7.0) | 0.3 (as silver) |
| Silver Iodobromide Emulsion (AgI: 3 mol %, uniform AgI type, diameter corresponding to sphere: 0.3 μm, coefficient of variation of diameter corresponding to sphere: 30%, tabular grain, diameter/thickness ratio: 7.0) | 0.15 (as silver) |
| Gelatin | 1.8 |
| ExS-6 | $9 \times 10^{-4}$ |
| ExC-1 | 0.06 |
| ExC-4 | 0.03 |
| ExY-9 | 0.14 |
| ExY-11 | 0.89 |
| Solv-1 | 0.42 |
| Thirteenth Layer: Intermediate Layer | |
| Gelatin | 0.7 |
| ExY-12 | 0.20 |
| Solv-1 | 0.34 |
| Fourteenth Layer: High-Speed Blue-sensitive Emulsion Layer | |
| Silver Iodobromide Emulsion (AgI: 10 mol %, internal high AgI type, diameter corresponding to sphere: 1.0 μm, coefficient of variation of diameter corresponding to sphere: 25%, multiple twin tabular grain, diameter/thickness ratio: 2.0 | 0.5 (as silver) |
| Gelatin | 0.5 |
| ExS-6 | $1 \times 10^{-4}$ |
| ExY-9 | 0.01 |
| ExY-11 | 0.20 |
| ExC-1 | 0.02 |
| Solv-1 | 0.10 |
| Fifteenth Layer: First Protective Layer | |
| Fine Grain Silver Iodobromide Emulsion (AgI: 2 mol %, uniform AgI type, diameter corresponding to sphere: 0.07 μm) | 0.12 (as silver) |
| Gelatin | 0.9 |
| UV-4 | 0.11 |
| UV-5 | 0.16 |
| Solv-5 | 0.02 |
| H-1 | 0.13 |
| Cpd-5 | 0.10 |
| Polyethyl Acrylate Latex | 0.09 |
| Sixteenth Layer: Second Protective Layer | |
| Fine grain Silver Iodobromide Emulsion (AgI: 2 mol %, uniform AgI type, diameter corresponding to sphere: 0.07 μm) | 0.36 (as silver) |
| Gelatin | 0.55 |
| Polymethyl Methacrylate Particle (diameter: 1.5 μm) | 0.2 |
| H-1 | 0.17 |

Each layer described above further contained a stabilizer for the emulsion (Cpd-3: 0.07 g/m²) and a surface active agent (Cpd-4: 0.03 g/m²) as a coating aid in addition to the above-described components.

The components used for the preparation of the light-sensitive material are shown below.

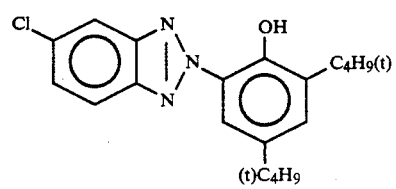

UV-1

-continued
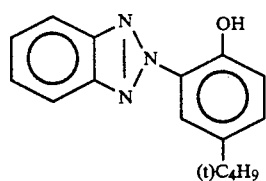  UV-2
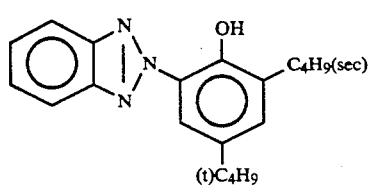  UV-3
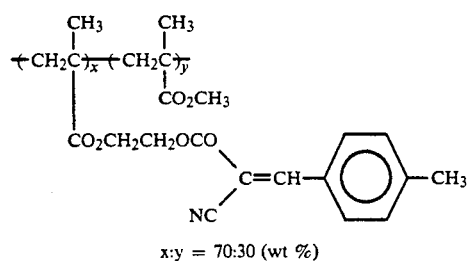  UV-4
x:y = 70:30 (wt %)
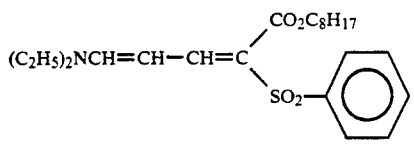  UV-5
Tricresyl phosphate  Solv-1
Dibutyl phthalate  Solv-2
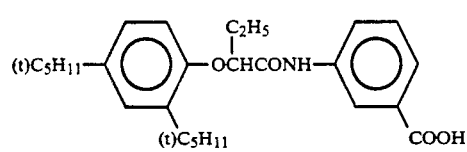  Solv-4
Trihexyl phosphate  Solv-5
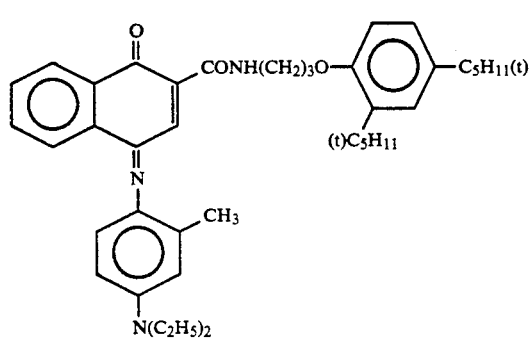  ExF-1

-continued
ExF-2
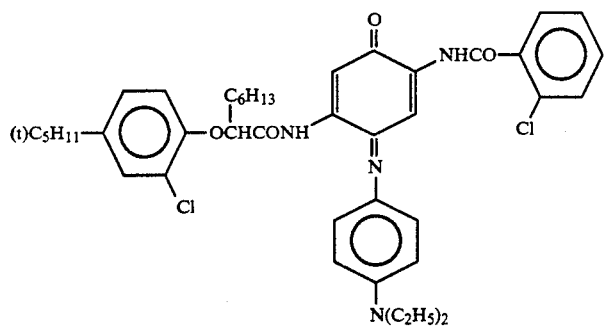
ExS-1
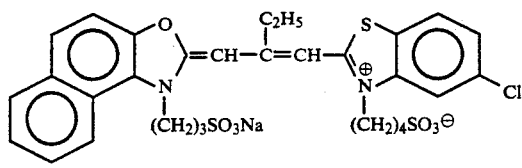
ExS-2
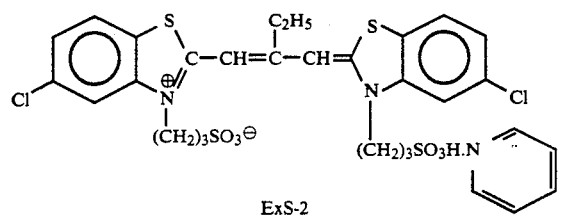
ExS-3
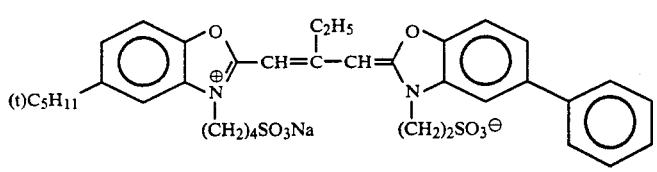
ExS-4
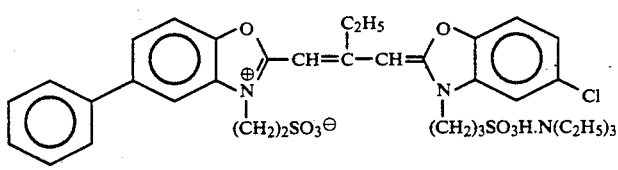
ExS-5
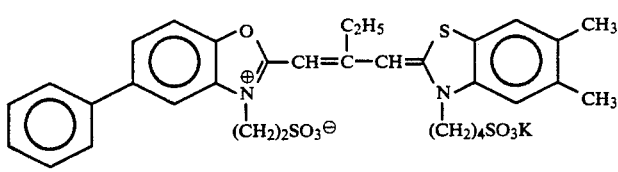
ExS-6
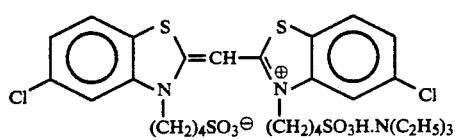
ExS-7
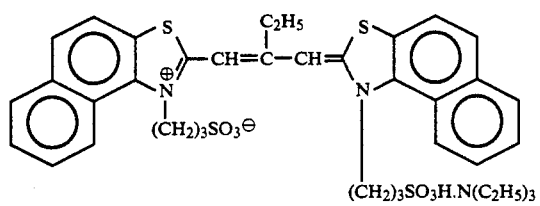

-continued
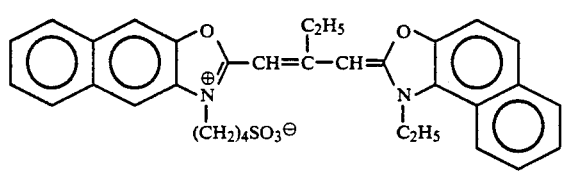
ExS-8
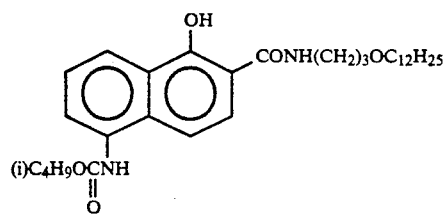
ExC-1
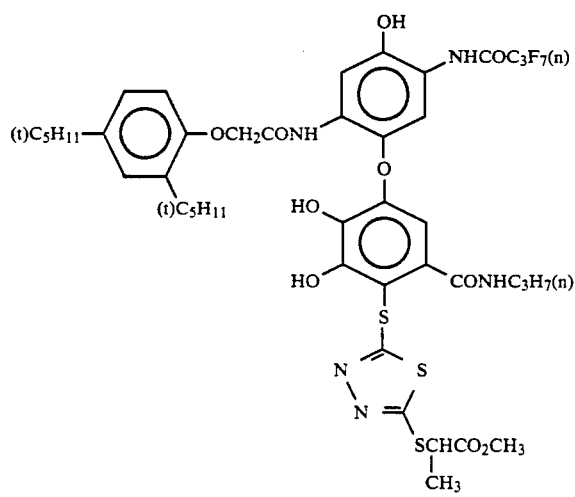
ExC-2
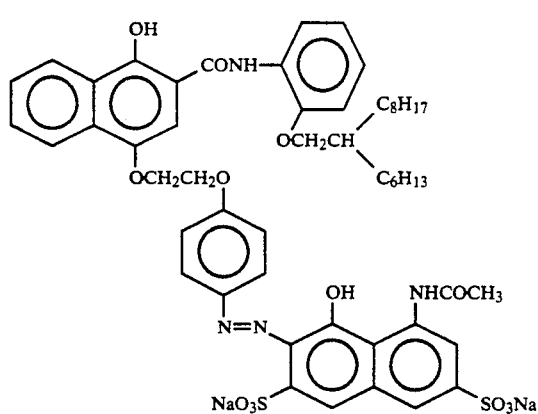
ExC-3
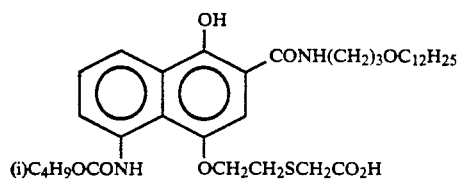
ExC-4

-continued
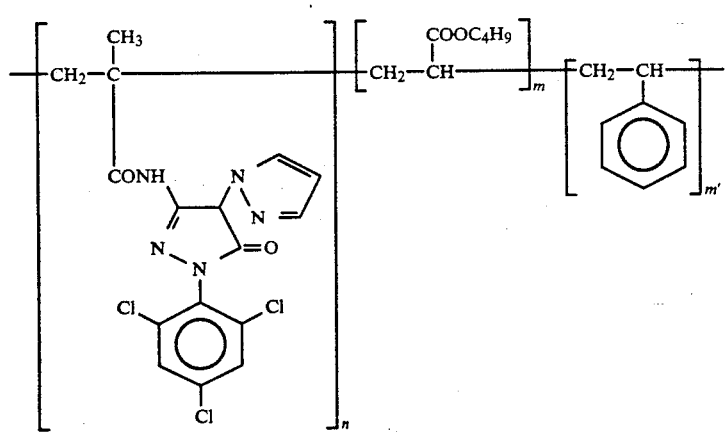
ExM-5
n = 50 (wt %)
m = 25 (wt %)
m' = 25 (wt %)
mol. wt. about 20,000
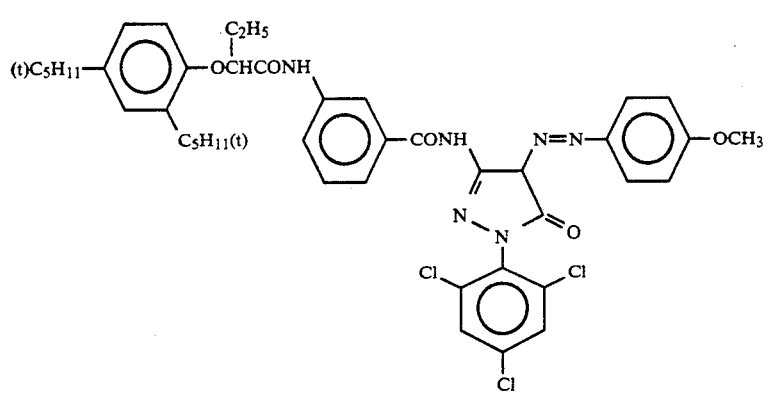
ExM-6
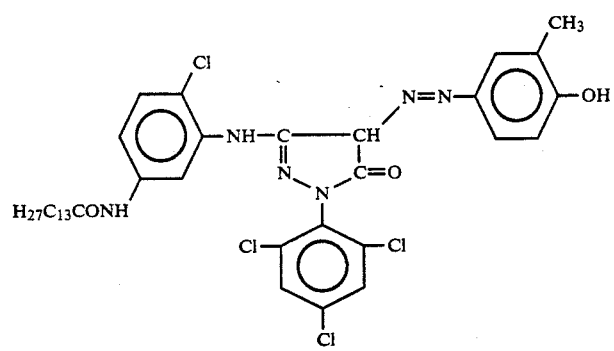
ExM-7
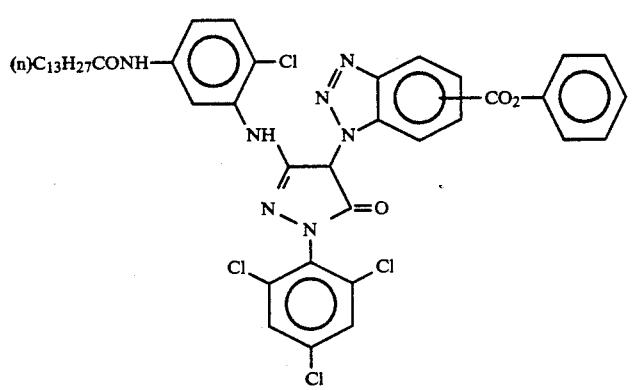
ExM-10

-continued
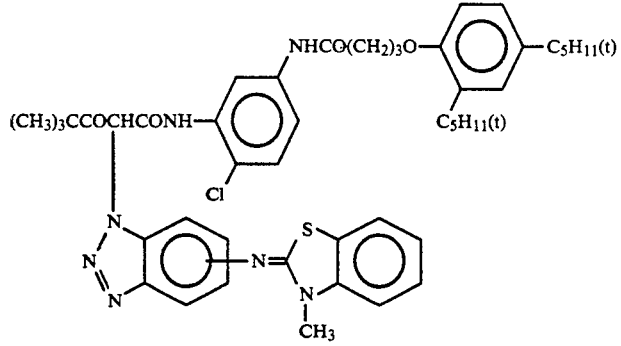
ExY-8
(coupler as described in U.S. Pat. No. 4,477,563)
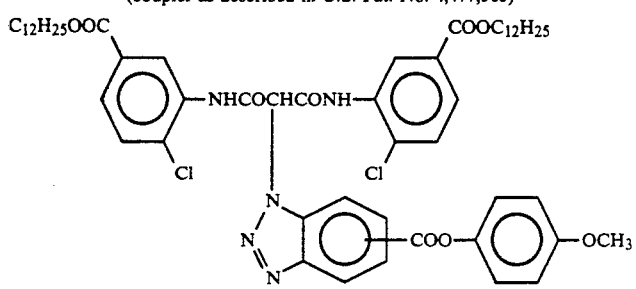
ExY-9
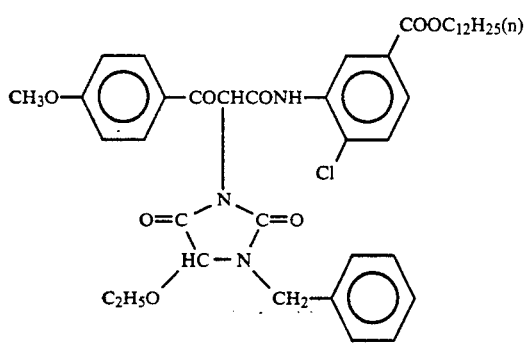
ExY-11
(coupler as described in U.S. Pat. No. 4,477,563)
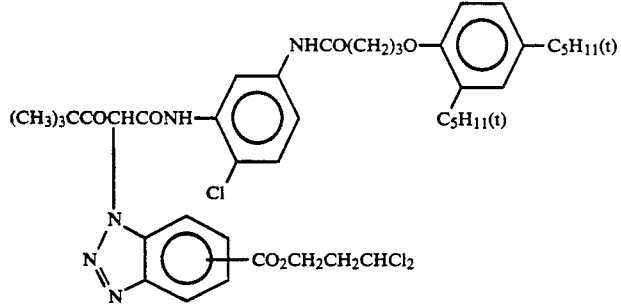
ExY-12
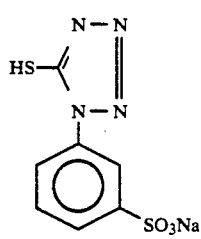
Cpd-7

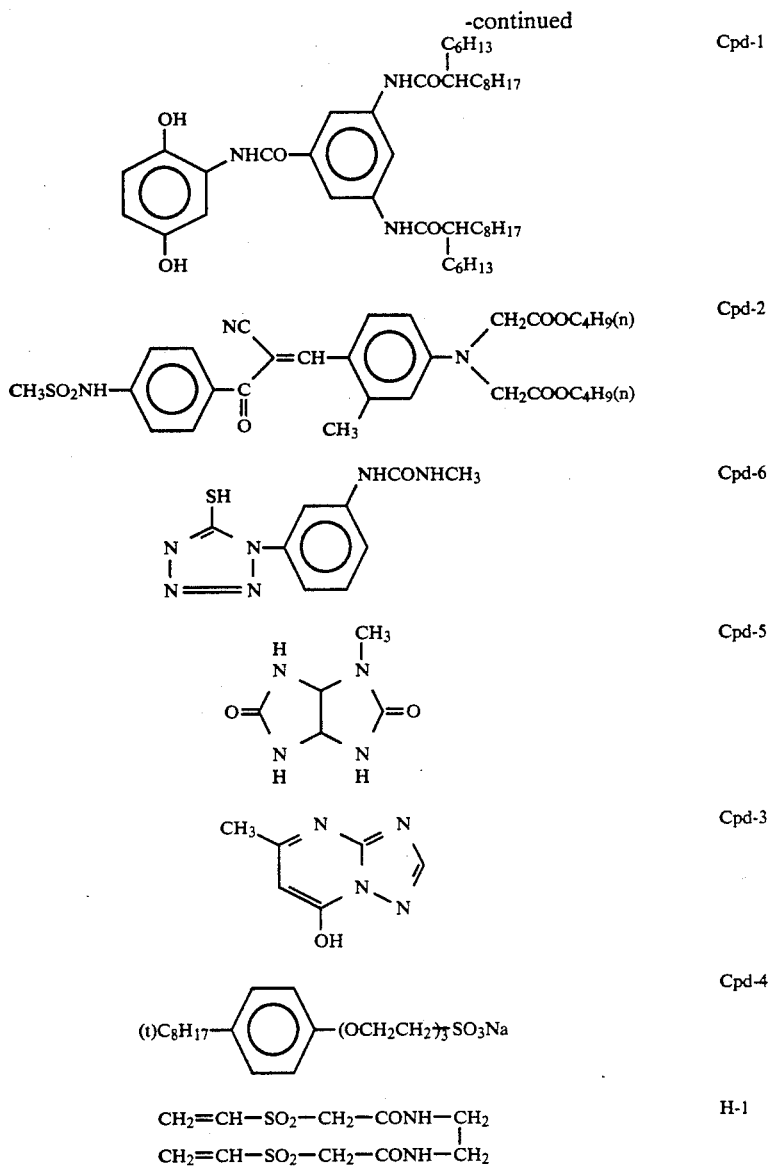

Preparation of Samples 102 to 108

Samples 102 to 108 were prepared in the same manner as described above for Sample 101 except for changing ExY-9 and ExY-12 added to the twelfth layer, the thirteenth layer and the fourteenth layer of Sample 101 to the couplers described in Table 1 shown below.

Each of the samples thus-prepared was cut into a 35 m/m width strip, and evaluated in the following manner.

(1) The sample was imagewise exposed to white light, subjected to development processing described below, and then the relative sensitivity of a yellow image at the density of fog +0.2 was determined.

(2) The sample was exposed to light for measuring the MTF value, subjected to the same development processing as described in (1), and then the MTF value of the yellow color image was determined in a conventional manner.

(3) The sample was uniformly exposed to green light, then imagewise exposed to blue light, and subjected to the same development processing as described in (1). The value which was obtained by subtracting the magenta density at the unexposed area to the blue light from the magenta density at the area having the exposure amount necessary for obtaining a yellow density of fog +1.0 was determined to evaluate the interlayer effect.

The color development processing steps employed and the comparative compounds used are described below.

| Processing Step | Processing Time | Processing Temperature (°C.) |
|---|---|---|
| Color Development | 3 min. 15 sec. | 38 |
| Bleaching | 1 min. 00 sec. | 38 |
| Bleach-Fixing | 3 min. 15 sec. | 38 |
| Washing with Water (1) | 40 sec. | 35 |
| Washing with Water (2) | 1 min. 00 sec. | 35 |
| Stabilizing | 40 sec. | 38 |
| Drying | 1 min. 15 sec. | 55 |

The composition of each processing solution used is illustrated below.

| Color Developing Solution: | |
|---|---|
| Diethylenetriaminepentaacetic Acid | 1.0 g |
| 1-Hydroxyethylidene-1,1-diphosphonic Acid | 3.0 g |
| Sodium Sulfite | 4.0 g |
| Potassium Carbonate | 30.0 g |
| Potassium Bromide | 1.4 g |
| Potassium Iodide | 1.5 mg |
| Hydroxylamine Sulfate | 2.4 g |
| 4-(N-Ethyl-N-$\beta$-hydroxyethylamino)-2-methylaniline Sulfate | 4.5 g |
| Water to make | 1.0 l |
| pH | 10.05 |
| Bleaching Solution: | |
| Ammonium Ethylenediaminetetraacetato Ferrate Dihydrate | 120.0 g |
| Disodium Ethylenediaminetetraacetate | 10.0 g |
| Ammonium Bromide | 100.0 g |
| Ammonium Nitrate | 10.0 g |
| Bleach Accelerating Agent | 0.005 mol |

$$\left[\left(\begin{matrix}H_3C\\ \phantom{H_3C}\diagdown\\ \phantom{H_3C}\phantom{.}N-CH_2-CH_2-S\\ \phantom{H_3C}\diagup\\ H_3C\end{matrix}\right)_{\!2}\right]\cdot 2HCl$$

| | |
|---|---|
| Aqueous Ammonia (27%) | 15.0 ml |
| Water to make | 1.0 l |
| pH | 6.3 |
| Bleach-Fixing Solution: | |
| Ammonium Ethylenediaminetetraacetato Ferrate Dihydrate | 50.0 g |
| Disodium Ethylenediaminetetraacetate | 5.0 g |
| Sodium Sulfite | 12.0 g |
| Ammonium thiosulfate (70% aq. soln) | 240.0 ml |
| Aqueous ammonia (27%) | 6.0 ml |
| Water to make | 1.0 l |
| pH | 7.2 |

Washing Water:

City water was passed through a mixed bed type column filled with an H type strong acidic cation exchange resin (Amberlite IR-120B manufactured by Rohm & Haas Co.) and an OH type anion exchange resin (Amberlite IR-400 manufactured by Rohm & Haas Co.) to prepare water containing not more than 3 mg/l of calcium ion and magnesium ion. To the water thus-treated were added sodium dichloroisocyanulate in an amount of 20 mg/l and sodium sulfate in an amount of 150 mg/l. The pH of the solution was in a range from 6.5 to 7.5.

| Stabilizing Solution: | |
|---|---|
| Formaldehyde (37% aq. soln.) | 2.0 ml |
| Polyoxyethylene-p-monononylphenylether (average degree of polymerization: 10) | 0.3 g |
| Disodium Ethylenediaminetetraacetate | 0.05 g |
| Water to make | 1.0 l |
| pH | 5.0 to 8.0 |

Comparative Couplers

ExY-13 (coupler as described in U.S. Pat. No. 4,248,962)

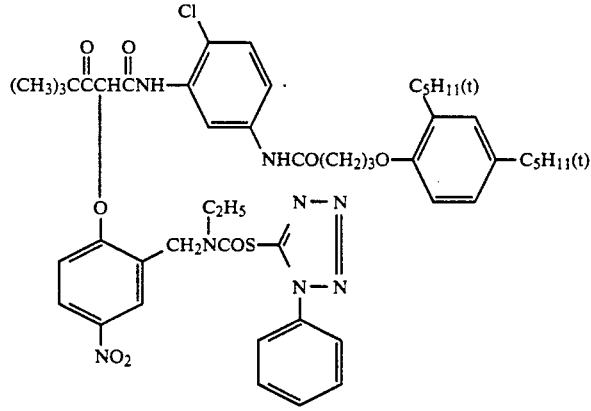

ExY-14 (coupler as described in JP-A-60-203943)

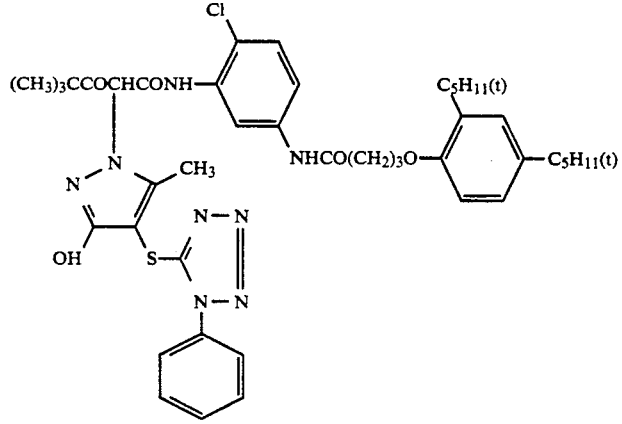

ExY-15 (coupler as described in JP-A-60-203943)

-continued
Comparative Couplers
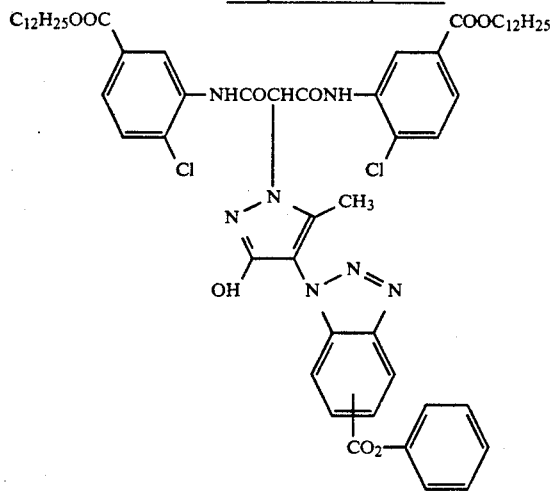
ExY-16 (coupler as described in JP-A-62-291645)
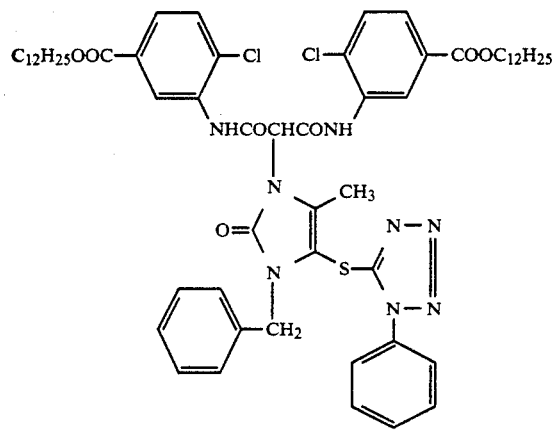
ExY-17 (coupler as described in JP-A-62-291645)
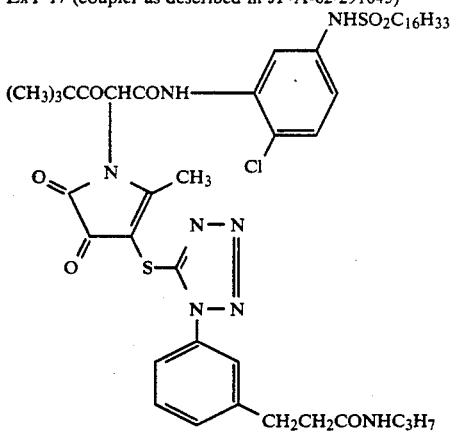
TABLE 1
| Sample No. | DIR Coupler or Coupler according to Present Invention | | | Relative** Sensitivity | MTF Value (20 c/mm) | Interlayer Effect |
| --- | --- | --- | --- | --- | --- | --- |
| | 12th Layer (Amount*) | 13th Layer (Amount*) | 14th Layer (Amount*) | | | |
| 101 (Comparison) | ExY-9 (1.0) | ExY-12 (1.0) | ExY-9 (1.0) | 100 | 0.78 | +0.06 |
| 102 (Comparison) | ExY-9 (1.0) | ExY-13 (0.02) | ExY-9 (1.0) | 98 | 0.76 | +0.09 |
| 103 (Comparison) | ExY-15 (1.5) | ExY-14 (0.05) | ExY-15 (1.5) | 102 | 0.80 | +0.06 |

TABLE 1-continued

| Sample No. | DIR Coupler or Coupler according to Present Invention | | | Relative** Sensitivity | MTF Value (20 c/mm) | Interlayer Effect |
| --- | --- | --- | --- | --- | --- | --- |
| | 12th Layer (Amount*) | 13th Layer (Amount*) | 14th Layer (Amount*) | | | |
| 104 (Comparison) | ExY-16 (0.5) | ExY-17 (1.0) | ExY-16 (0.5) | 100 | 0.81 | +0.04 |
| 105 (Present Invention) | (1) (1.0) | (2) (1.0) | (1) (1.0) | 100 | 0.83 | ±0.00 |
| 106 (Present Invention) | (3) (1.0) | (5) (1.5) | (3) (1.0) | 98 | 0.82 | ±0.01 |
| 107 (Present Invention) | (6) (1.5) | (9) (1.0) | (6) (1.5) | 100 | 0.83 | ±0.00 |
| 108 (Present Invention) | (8) (1.5) | (14) (1.0) | (8) (1.5) | 100 | 0.83 | ±0.00 |

*The molar ratio taking the amount of DIR coupler used in Sample 101 as 1.0 (the amount was adjusted to obtain almost the same sensitivity and gradation)
**Relative value taking the exposure amount necessary for obtaining a density of fog ±0.2 in Sample 101 as 100.

From the results shown in Table 1 above, it is clear that the samples using the couplers according to the present invention have excellent sharpness and interlayer effect.

EXAMPLE 2

On a cellulose triacetate film support provided with a subbing layer was coated each layer having the composition set forth below to prepare a multilayer color photographic light-sensitive material, which was designated Sample 201.

In the compositions of the layers, the coating amounts are shown in units of g/m$^2$, coating amounts of silver halide are shown in terms of silver coating amount in units of g/m$^2$, and those of the sensitizing dyes are shown as a molar amount per mol of silver halide present in the same layer.

| | |
| --- | --- |
| First Layer: Antihalation Layer | |
| Black Colloidal Silver | 0.18 (as silver) |
| Gelatin | 0.40 |
| Second Layer: Intermediate Layer | |
| 2,5-Di-tert-pentadecylhydroquinone | 0.18 |
| EX-1 | 0.07 |
| EX-3 | 0.02 |
| EX-12 | 0.002 |
| U-1 | 0.06 |
| U-2 | 0.08 |
| U-3 | 0.10 |
| HBS-1 | 0.10 |
| HBS-2 | 0.02 |
| Gelatin | 1.04 |
| Third Layer: First Red-Sensitive Emulsion Layer | |
| Emulsion A | 0.25 (as silver) |
| Emulsion B | 0.25 (as silver) |
| Sensitizing Dye I | 6.9 × 10$^{-5}$ |
| Sensitizing Dye II | 1.8 × 10$^{-5}$ |
| Sensitizing Dye III | 3.1 × 10$^{-5}$ |
| EX-2 | 0.335 |
| EX-10 | 0.020 |
| HBS-1 | 0.060 |
| Gelatin | 0.87 |
| Fourth Layer: Second Red-Sensitive Emulsion Layer | |
| Emulsion G | 1.0 (as silver) |
| Sensitizing Dye I | 5.1 × 10$^{-5}$ |
| Sensitizing Dye II | 1.4 × 10$^{-5}$ |
| Sensitizing Dye III | 2.3 × 10$^{-4}$ |
| EX-2 | 0.400 |
| EX-3 | 0.050 |
| EX-10 | 0.015 |
| HBS-1 | 0.060 |
| Gelatin | 1.30 |
| Fifth Layer: Third Red-Sensitive Emulsion Layer | |
| Emulsion D | 1.60 (as silver) |
| Sensitizing Dye I | 5.4 × 10$^{-5}$ |
| Sensitizing Dye II | 1.4 × 10$^{-5}$ |
| Sensitizing Dye III | 2.4 × 10$^{-4}$ |
| EX-3 | 0.010 |
| EX-4 | 0.080 |
| EX-2 | 0.097 |
| HBS-1 | 0.22 |
| HBS-2 | 0.10 |
| Gelatin | 1.63 |
| Sixth Layer: Intermediate Layer | |
| EX-5 | 0.040 |
| HBS-1 | 0.020 |
| Gelatin | 0.80 |
| Seventh Layer: First Green-Sensitive Emulsion Layer | |
| Emulsion A | 0.15 (as silver) |
| Emulsion B | 0.15 (as silver) |
| Sensitizing Dye V | 3.0 × 10$^{-5}$ |
| Sensitizing Dye VI | 1.0 × 10$^{-5}$ |
| Sensitizing Dye VII | 3.8 × 10$^{-4}$ |
| EX-6 | 0.260 |
| EX-1 | 0.021 |
| EX-7 | 0.030 |
| EX-14 | 0.012 |
| HBS-1 | 0.100 |
| HBS-3 | 0.010 |
| Gelatin | 0.63 |
| Eighth Layer: Second Green-Sensitive Emulsion Layer | |
| Emulsion C | 0.45 (as silver) |
| Sensitizing Dye V | 2.1 × 10$^{-5}$ |
| Sensitizing Dye VI | 7.0 × 10$^{-5}$ |
| Sensitizing Dye VII | 2.6 × 10$^{-4}$ |
| EX-6 | 0.094 |
| EX-14 | 0.008 |
| EX-7 | 0.026 |
| HBS-1 | 0.160 |
| HBS-3 | 0.008 |
| Gelatin | 0.50 |
| Ninth Layer: Third Green-Sensitive Emulsion Layer | |
| Emulsion E | 1.2 (as silver) |
| Sensitizing Dye V | 3.5 × 10$^{-5}$ |
| Sensitizing Dye VI | 8.0 × 10$^{-5}$ |
| Sensitizing Dye VII | 3.0 × 10$^{-4}$ |
| EX-13 | 0.015 |
| EX-11 | 0.100 |
| EX-1 | 0.025 |
| HBS-1 | 0.25 |

-continued

| | |
|---|---|
| HBS-2 | 0.10 |
| Gelatin | 1.54 |
| Tenth Layer: Yellow Filter Layer | |
| Yellow Colloidal Silver | 0.05 (as silver) |
| EX-5 | 0.08 |
| HBS-1 | 0.03 |
| Gelatin | 0.95 |
| Eleventh Layer: First Blue-Sensitive Emulsion Layer | |
| Emulsion A | 0.08 (as silver) |
| Emulsion B | 0.07 (as silver) |
| Emulsion F | 0.07 (as silver) |
| Sensitizing Dye VIII | $3.5 \times 10^{-4}$ |
| EX-9 | 0.721 |
| EX-8 | 0.042 |
| HBS-1 | 0.28 |
| Gelatin | 1.10 |
| Twelfth Layer: Second Blue-Sensitive Emulsion Layer | |
| Emulsion G | 0.45 (as silver) |
| Sensitizing Dye VIII | $2.1 \times 10^{-4}$ |
| EX-9 | 0.154 |
| EX-10 | 0.007 |
| HBS-1 | 0.05 |

-continued

| | |
|---|---|
| Gelatin | 0.78 |
| Thirteenth Layer: Third Blue-Sensitive Emulsion Layer | |
| Emulsion H | 0.77 (as silver) |
| Sensitizing Dye VIII | $2.2 \times 10^{-4}$ |
| EX-9 | 0.20 |
| HBS-1 | 0.07 |
| Gelatin | 0.69 |
| Fourteenth Layer: First Protective Layer | |
| Emulsion I | 0.5 (as silver) |
| U-4 | 0.11 |
| U-5 | 0.17 |
| HBS-1 | 0.05 |
| Gelatin | 1.00 |
| Fifteenth Layer: Second Protective Layer | |
| Polymethyl methacrylate particle (diameter: about 1.5 μm) | 0.54 |
| S-1 | 0.20 |
| Gelatin | 1.20 |

Gelatin Hardener H-1 and a surface active agent were added to each of the layers in addition to the above described components.

| Emulsion | Average AgI Content (%) | Average Particle Diameter (μm) | Coefficient of Variation on Particle Diameter (%) | Diameter/ Thickness Ratio | Ratio of Silver Amount (AgI Content %) |
|---|---|---|---|---|---|
| A | 4.1 | 0.45 | 27 | 1 | Double Structure Grain Core/Shell = 1/3 (13/1) |
| B | 8.9 | 0.70 | 14 | 1 | Double Structure Grain Core/Shell = 3/7 (25/2) |
| C | 10 | 0.75 | 30 | 2 | Double Structure Grain Core/Shell = 1/2 (24/3) |
| D | 16 | 1.05 | 35 | 2 | Double Structure Grain Core/Shell = 1/2 (40/0) |
| E | 10 | 1.05 | 35 | 3 | Double Structure Grain Core/Shell = 1/2 (24/3) |
| F | 4.1 | 0.25 | 28 | 1 | Double Structure Grain Core/Shell = 1/3 (13/1) |
| G | 13.6 | 0.75 | 25 | 2 | Double Structure Grain Core/Shell = 1/2 (40/0) |
| H | 14 | 1.30 | 25 | 3 | Double Structure Grain Core/Shell = 37/63 (34/3) |
| I | 1 | 0.07 | 15 | 1 | Uniform Grain |

The components employed for the preparation of the above light-sensitive materials are shown below.

EX-1

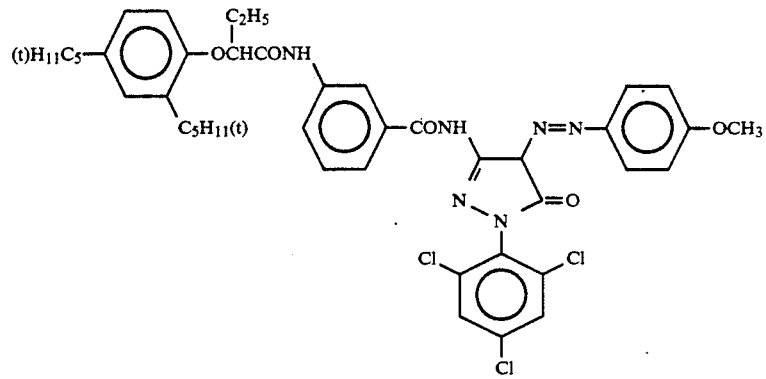

EX-2

-continued
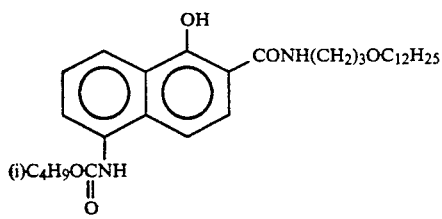
EX-3
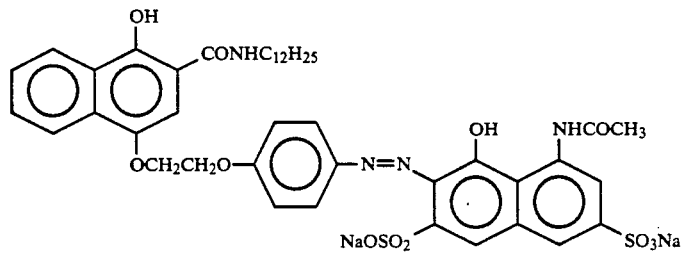
EX-4
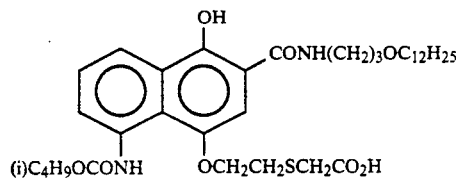
EX-5
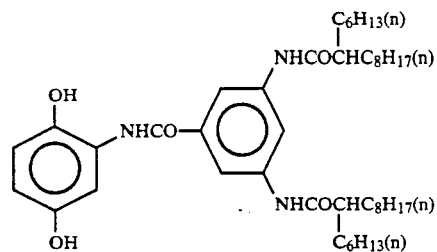
EX-6
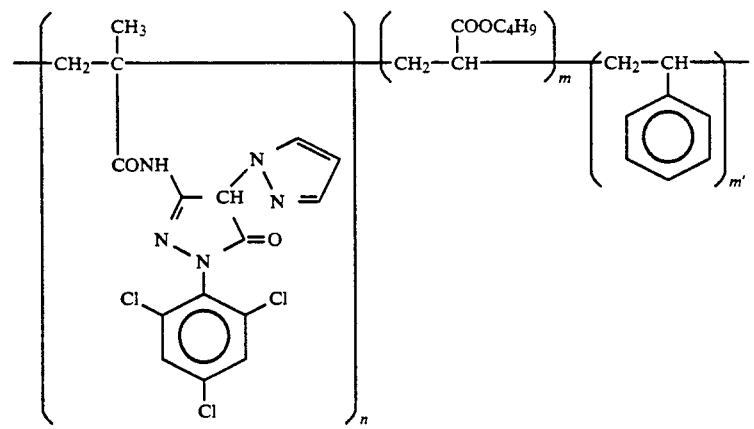
n = 50 (wt %)
m = 25 (wt %)
n' = 25 (wt %)
mol. wt. about 20,000
EX-7

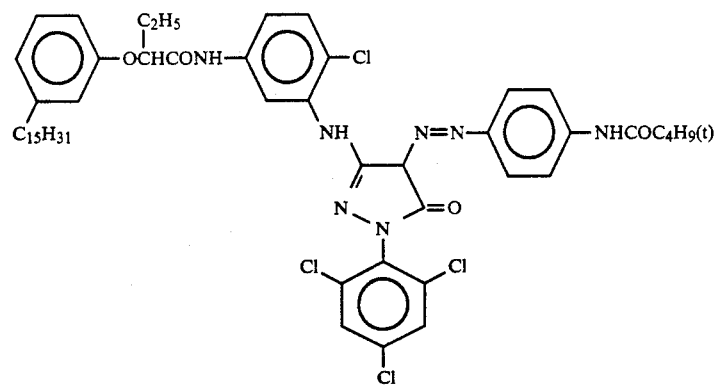
EX-8
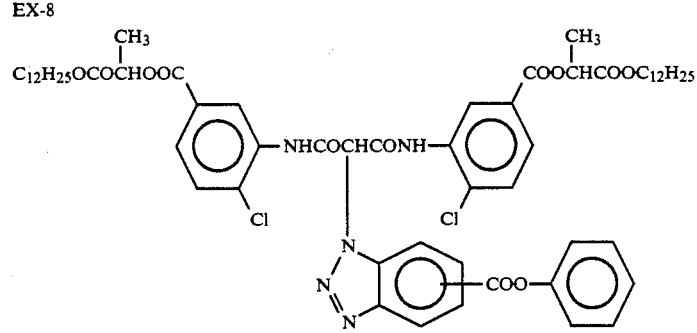
EX-9
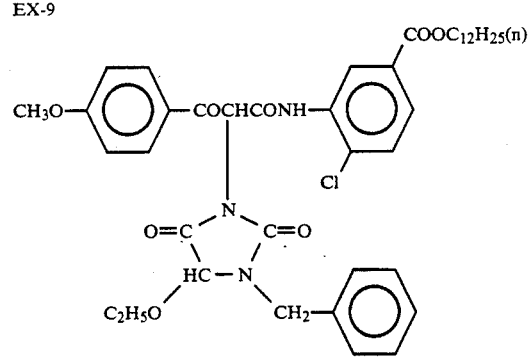
EX-10
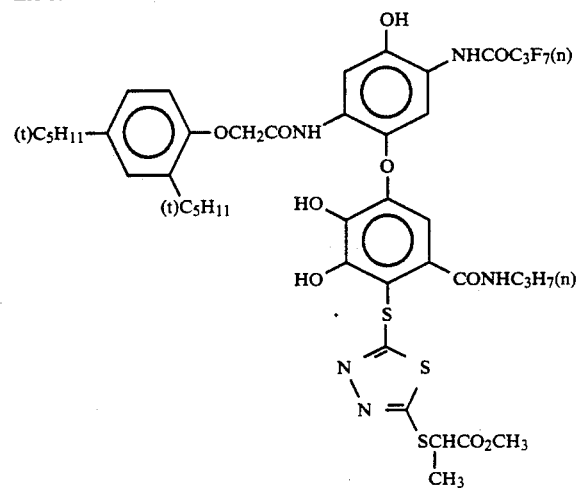
EX-11

-continued
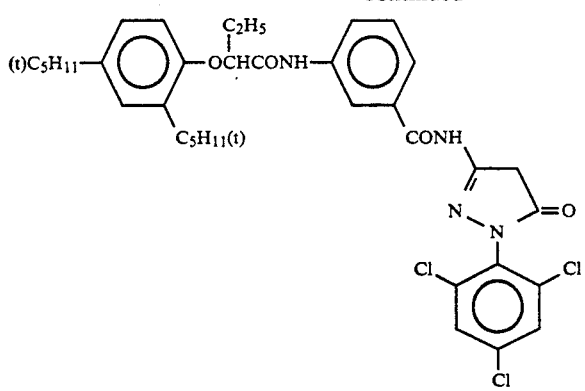
EX-12
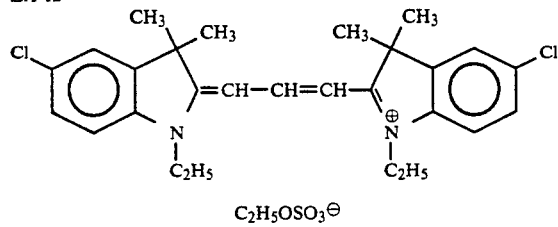
EX-13
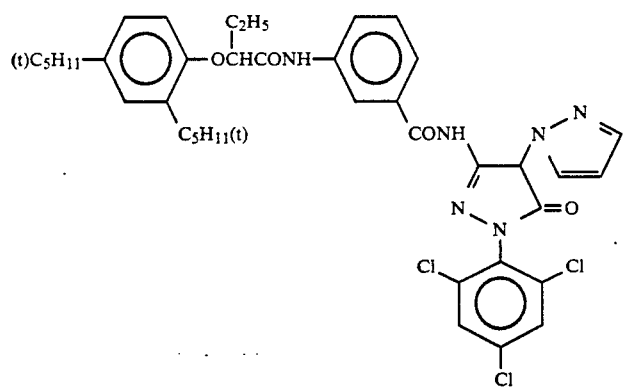
U-1
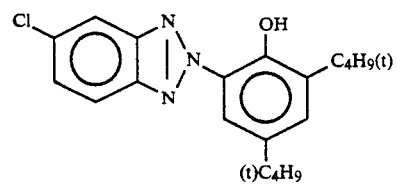
U-2
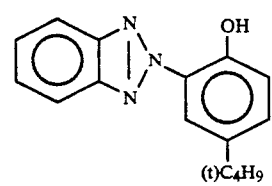
U-3
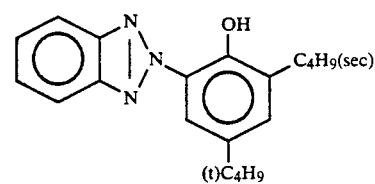

U-4
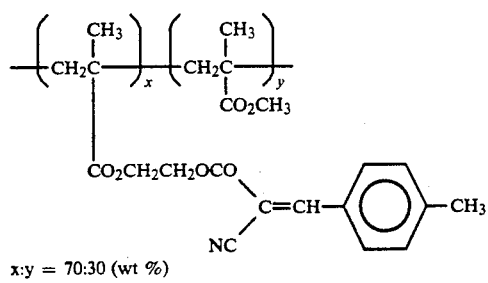
x:y = 70:30 (wt %)
U-5
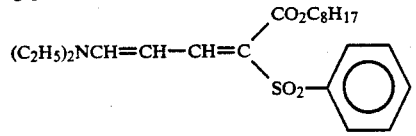
HBS-1
Tricresyl phosphate
HBS-2
Di-n-butyl phthalate
HBS-3
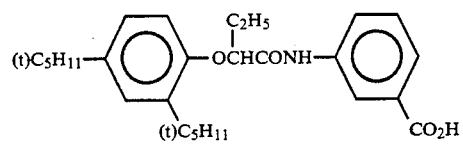
Sensitizing Dye I
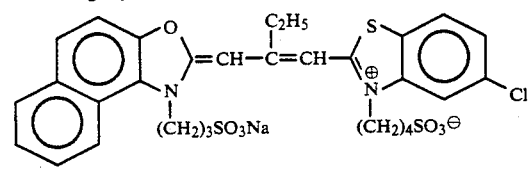
Sensitizing Dye II
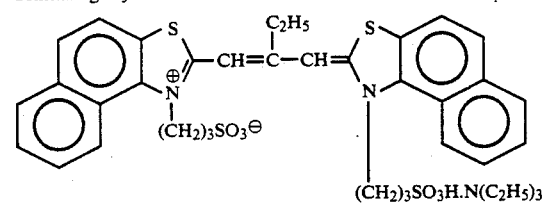
Sensitizing Dye III
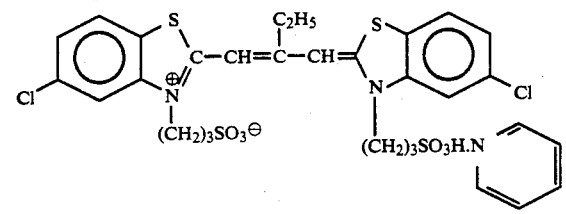
Sensitizing Dye V
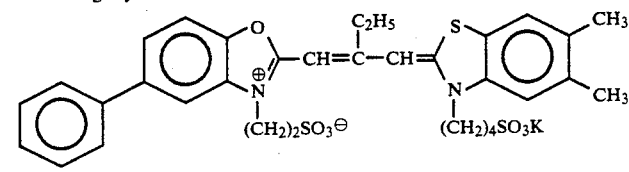
Sensitizing Dye VI -continued

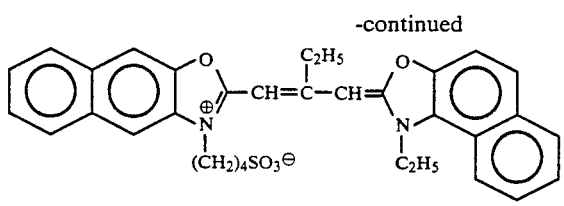

Sensitizing Dye VII

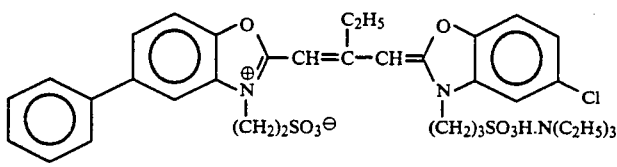

Sensitizing Dye VIII

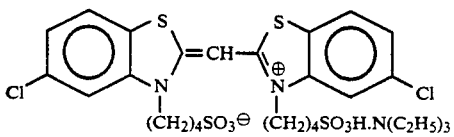

S-1

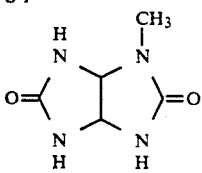

H-1

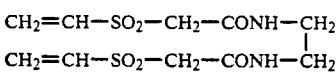

Compatative Coupler
EX-14
(analogous coupler to that described in U.S.
Pat. No. 4,338,393)

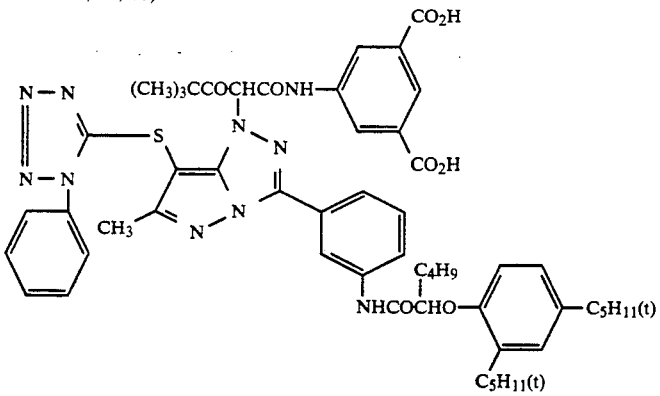

Preparation of Samples 202 and 203

Samples 202 and 203 were prepared in the same manner as described for Sample 201 except for changing EX-14 added to the seventh layer and the eighth layer of Sample 201 to the couplers described in Table 2 below.

TABLE 2

| Sample No. | DIR Coupler Used in Seventh Layer and Eighth Layer |
|---|---|
| 201 (Comparison) | EX-14 |
| 202 (Present Invention) | (11) |
| 203 (Present Invention) | (12) |

Each of the samples thus-prepared was cut into a 35 m/m width strip, photographed conventionally and then subjected to development processing as described in Example 1 or development processing described below.

It was found that Sample 202 and 203 using the couplers according to the present invention exhibited excellent sharpness and color reproducibility upon any of development processing.

| Processing Step | Processing Time | Processing Temperature (°C.) |
|---|---|---|
| Color Development | 2 min. 30 sec. | 40 |
| Bleach-fixing | 3 min. 00 sec. | 40 |
| Washing with Water (1) | 20 sec. | 35 |
| Washing with Water (2) | 20 sec. | 35 |
| Stabilizing | 20 sec. | 35 |
| Drying | 50 sec. | 65 |

The composition of each processing solution used is illustrated below.

| Color Developing Solution: | |
|---|---|
| Diethylenetriaminepentaacetic Acid | 2.0 g |
| 1-Hydroxyethylidene-1,1-diphosphonic Acid | 3.0 g |
| Sodium Sulfite | 4.0 g |
| Potassium Carbonate | 30.0 g |
| Potassium Bromide | 1.4 g |
| Potassium Iodide | 1.5 mg |
| Hydroxylamine Sulfate | 2.4 g |
| 4-[N-Ethyl-N-($\beta$-hydroxyethyl)amino]-2-methylaniline Sulfate | 4.5 g |
| Water to make | 1.0 l |
| pH | 10.05 |
| Bleach-Fixing Solution: | |
| Ammonium Ethylenediaminetetraacetato Ferrate Dihydrate | 50.0 g |
| Disodium Ethylenediaminetetraacetate | 5.0 g |
| Sodium Sulfite | 12.0 g |
| Ammonium Thiosulfate (70% aqueous solution) | 260.0 ml |
| Acetic Acid (98%) | 5.0 ml |
| Bleach Accelerating Agent | 0.01 mol |

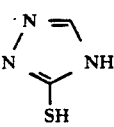

| | |
|---|---|
| Water to make | 1.0 l |
| pH | 6.0 |

Washing Water:

City water was passed through a mixed bed type column filled with an H type strong acidic cation exchange resin (Amberlite IR-120B manufactured by Rohm & Haas Co.) and an OH type anion exchange resin (Amberlite IRA400 manufactured by Rohm & Haas Co.) to prepare water containing not more than 3 mg/l of calcium ion and magnesium ion. To the water thus-treated were added sodium dichloroisocyanurate in an amount of 20 mg/l and sodium sulfate in an amount of 1.5 g/l. The pH of the solution was in the range from 6.5 to 7.5.

| Stabilizing Solution: | |
|---|---|
| Formaldehyde (37% aq. soln.) | 2.0 ml |
| Polyoxyethylene-p-monononylphenylether (average degree of polymerization: 10) | 0.3 g |
| Disodium Ethylenediaminetetraacetate | 0.05 g |
| Water to make | 1.0 l |

| Stabilizing Solution: | |
|---|---|
| pH | 5.0 to 8.0 |

EXAMPLE 3

On a cellulose triacetate film support provided with a subbing layer was coated each layer having the composition set forth below to prepare a multilayer color photographic light-sensitive material, which was designated Sample 301.

In the compositions of the layers, the coating amounts of silver halide and colloidal silver are shown as g/m² units in terms of silver, those of the couplers, additives and gelatin are shown as g/m² unites, and those of the sensitizing dyes are shown as the molar amount per mol of silver halide present in the same layer.

| First Layer: Antihalation Layer | |
|---|---|
| Black Colloidal Silver | 0.2 (as silver) |
| Gelatin | 2.2 |
| UV-1 | 0.1 |
| UV-2 | 0.2 |
| Cpd-1 | 0.05 |
| Solv-1 | 0.01 |
| Solv-2 | 0.01 |
| Solv-3 | 0.08 |
| Second Layer: Intermediate Layer | |
| Fine Grain Silver Bromide (diameter corresponding to sphere: 0.07 μm) | 0.15 (as silver) |
| Gelatin | 1.0 |
| Cpd-2 | 0.2 |
| Third Layer: First Red-Sensitive Emulsion Layer | |
| Silver Iodobromide Emulsion (silver iodide: 10.0 mol %; internal high silver iodide type; diameter corresponding to sphere: 0.7 μm; coefficient of variation of diameter corresponding to sphere: 14%; tetradecahedral grain) | 0.26 (as silver) |
| Silver Iodobromide Emulsion (silver iodide: 4.0 mol %; internal high silver iodide type; diameter corresponding to sphere: 0.4 μm; coefficient of variation of diameter corresponding to sphere: 22%; tetradecahedral grain) | 0.2 (as silver) |
| Gelatin | 1.0 |
| ExS-1 | $4.5 \times 10^{-4}$ |
| ExS-2 | $1.5 \times 10^{-4}$ |
| ExS-3 | $0.4 \times 10^{-4}$ |
| ExS-4 | $0.3 \times 10^{-4}$ |
| ExC-1 | 0.33 |
| ExC-2 (Compound (18)) | 0.009 |
| ExC-3 | 0.023 |
| ExC-6 | 0.14 |
| Fourth Layer: Second Red-Sensitive Emulsion Layer | |
| Silver Iodobromide Emulsion (silver iodide: 16 mol %; internal high silver iodide type; diameter corresponding to sphere: 1.0 μm; coefficient of variation of diameter corresponding to sphere: 25%; tabular grain; diameter/thickness ratio: 4.0) | 0.55 (as silver) |
| Gelatin | 0.7 |
| ExS-1 | $3 \times 10^{-4}$ |
| ExS-2 | $1 \times 10^{-4}$ |
| ExS-3 | $0.3 \times 10^{-4}$ |
| ExS-4 | $0.3 \times 10^{-4}$ |
| ExC-3 | 0.05 |
| ExC-4 | 0.10 |
| ExC-6 | 0.08 |
| Fifth Layer: Third Red-Sensitive Emulsion Layer | |
| Silver Iodobromide Emulsion (silver | 0.9 |

| | |
|---|---|
| iodide: 10.0 mol %; internal high silver iodide type; diameter corresponding to sphere: 1.2 μm; coefficient of variation of diameter corresponding to sphere: 28%; tabular grain; diameter/thickness ratio: 6.0) | (as silver) |
| Gelatin | 0.6 |
| ExS-1 | $2 \times 10^{-4}$ |
| ExS-2 | $0.6 \times 10^{-4}$ |
| ExS-3 | $0.2 \times 10^{-4}$ |
| ExC-4 | 0.07 |
| ExC-5 | 0.06 |
| Solv-1 | 0.12 |
| Solv-2 | 0.12 |
| Sixth Layer: Intermediate Layer | |
| Gelatin | 1.0 |
| Cpd-4 | 0.1 |
| Seventh Layer: First Green-Sensitive Emulsion Layer | |
| Silver Iodobromide Emulsion (silver iodide: 10.0 mol %; internal high silver iodide type; diameter corresponding to sphere: 0.7 μm; coefficient of variation of diameter corresponding to sphere: 14%; tetradecahedral grain) | 0.2 (as silver) |
| Silver Iodobromide Emulsion (silver iodide: 4.0 mol %; internal high silver iodide type; diameter corresponding to sphere: 0.4 μm; coefficient of variation of diameter corresponding to sphere: 22%; tetradecahedral grain) | 0.1 (as silver) |
| Gelatin | 1.2 |
| ExS-5 | $5 \times 10^{-4}$ |
| ExS-6 | $2 \times 10^{-4}$ |
| ExS-7 | $1 \times 10^{-4}$ |
| ExM-1 | 0.41 |
| ExM-2 | 0.10 |
| ExM-5 | 0.03 |
| Solv-1 | 0.2 |
| Solv-5 | 0.03 |
| Eighth Layer: Second Green-Sensitive Emulsion Layer | |
| Silver Iodobromide Emulsion (silver iodide: 10 mol %; internal high silver iodide type; diameter corresponding to sphere: 1.0 μm; coefficient of variation of diameter corresponding to sphere: 25%; tabular grain; diameter/thickness ratio: 3.0) | 0.4 (as silver) |
| Gelatin | 0.35 |
| ExS-5 | $3.5 \times 10^{-4}$ |
| ExS-6 | $1.4 \times 10^{-4}$ |
| ExS-7 | $0.7 \times 10^{-4}$ |
| ExM-1 | 0.09 |
| ExM-3 | 0.01 |
| Solv-1 | 0.15 |
| Solv-5 | 0.03 |
| Ninth Layer: Intermediate Layer | |
| Gelatin | 0.5 |
| Tenth Layer: Third Green-Sensitive Emulsion Layer | |
| Silver Iodobromide Emulsion (silver iodide: 10.0 mol %; internal high silver iodide type; diameter corresponding to sphere: 1.2 μm; coefficient of variation of diameter corresponding to sphere: 28%; tabular grain; diameter/thickness ratio: 6.0) | 1.0 (as silver) |
| Gelatin | 0.8 |
| ExS-5 | $2 \times 10^{-4}$ |
| ExS-6 | $0.8 \times 10^{-4}$ |
| ExS-7 | $0.8 \times 10^{-4}$ |
| ExM-3 | 0.01 |
| ExM-4 | 0.04 |
| ExC-4 | 0.005 |
| Solv-1 | 0.2 |
| Eleventh Layer: Yellow Filter Layer | |
| Cpd-3 | 0.05 |
| Gelatin | 0.5 |
| Solv-1 | 0.1 |
| Twelfth Layer: Intermediate Layer | |
| Gelatin | 0.5 |
| Cpd-2 | 0.1 |
| Thirteenth Layer: First Blue-Sensitive Emulsion Layer | |
| Silver Iodobromide Emulsion (silver iodide: 10 mol %; internal high silver iodide type; diameter corresponding to sphere: 0.7 μm; coefficient of variation of diameter corresponding to sphere: 14%; tetradecahedral grain) | 0.1 (as silver) |
| Silver Iodobromide Emulsion (silver iodide: 4.0 mol %; internal high silver iodide type; diameter corresponding to sphere: 0.4 μm; coefficient of variation of diameter corresponding to sphere: 22%; tetradecahedral grain) | 0.05 (as silver) |
| Gelatin | 1.0 |
| ExS-8 | $3 \times 10^{-4}$ |
| ExY-1 | 0.53 |
| ExY-2 | 0.02 |
| Solv-1 | 0.15 |
| Fourteenth Layer: Second Blue-Sensitive Emulsion Layer | |
| Silver Iodobromide Emulsion (silver iodide: 19.0 mol %; internal high silver iodide type; diameter corresponding to sphere: 1.0 μm; coefficient of variation of diameter corresponding to sphere: 16%; tetradecahedral grain) | 0.19 (as silver) |
| Gelatin | 0.3 |
| ExS-8 | $2 \times 10^{-4}$ |
| ExY-1 | 0.22 |
| Solv-1 | 0.07 |
| Fifteenth Layer: Intermediate Layer | |
| Fine Grain Silver Iodobromide (silver iodide: 12 mol %; uniform silver iodide type; diameter corresponding to sphere: 0.13 μm) | 0.2 (as silver) |
| gelatin | 0.36 |
| Sixteenth Layer: Third Blue-Sensitive Emulsion Layer | |
| Silver Iodobromide Emulsion (silver iodide: 14.0 mol %; internal high silver iodide type; diameter corresponding to sphere: 1.5 μm; coefficient of variation of diameter corresponding to sphere: 28%; tabular grain; diameter/thickness ratio: 5.0) | 1.0 (as silver) |
| Gelatin | 0.5 |
| ExS-8 | $1.5 \times 10^{-4}$ |
| ExY-1 | 0.2 |
| Solv-1 | 0.07 |
| Seventeenth Layer: First Protective Layer | |
| Gelatin | 1.8 |
| UV-1 | 0.1 |
| UV-2 | 0.2 |
| Solv-1 | 0.01 |
| Solv-2 | 0.01 |
| Eighteenth Layer: Second Protective Layer | |
| Fine Grain Silver Bromide (diameter corresponding to sphere: 0.07 μm) | 0.18 (as silver) |
| Gelatin | 0.7 |
| Polymethyl Methacrylate Particles (diameter: 1.5 μm) | 0.2 |
| W-1 | 0.02 |
| H-1 | 0.4 |
| Cpd-5 | 1.0 |

The components employed for the preparation of the light-sensitive materials above are shown below.

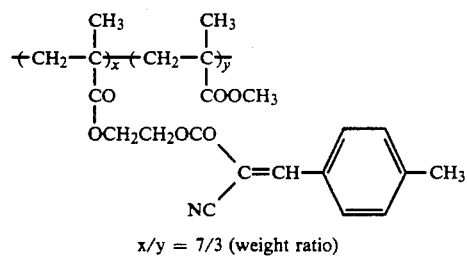
UV-1
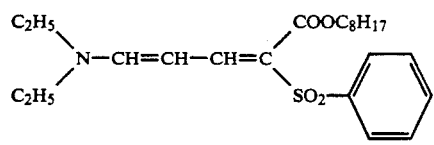
UV-2
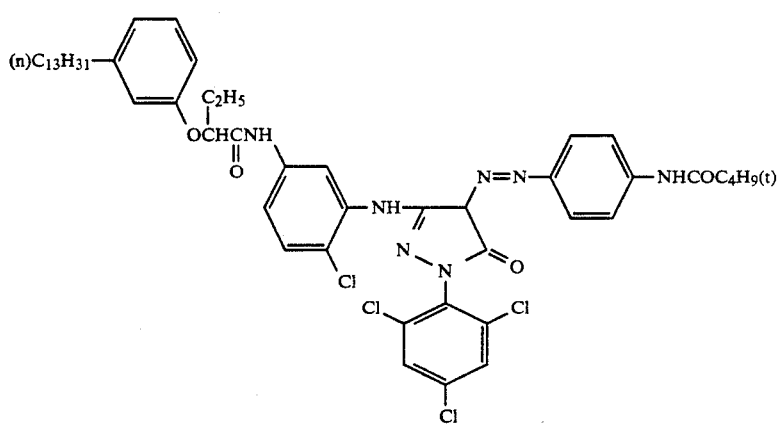
ExM-3
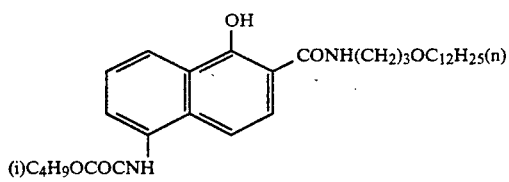
ExC-1
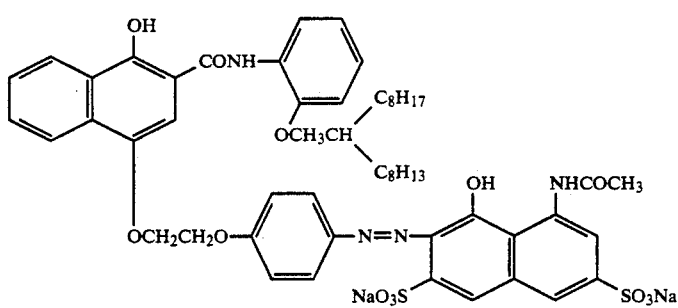
ExC-3
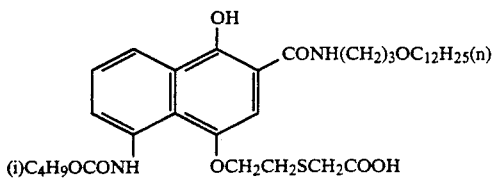
ExC-6

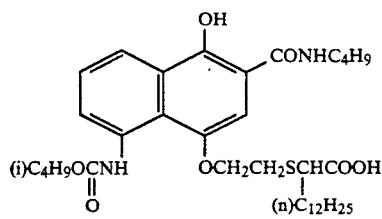
ExC-4
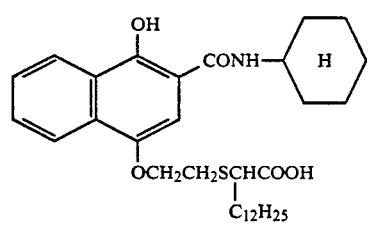
ExC-5
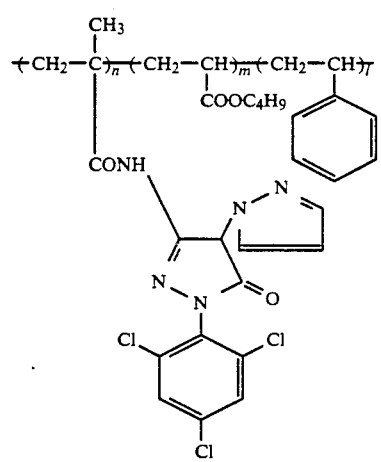
ExM-1
n:m:l = 2:1:1 (weight ratio)
Average Molecular Weight: 40,000
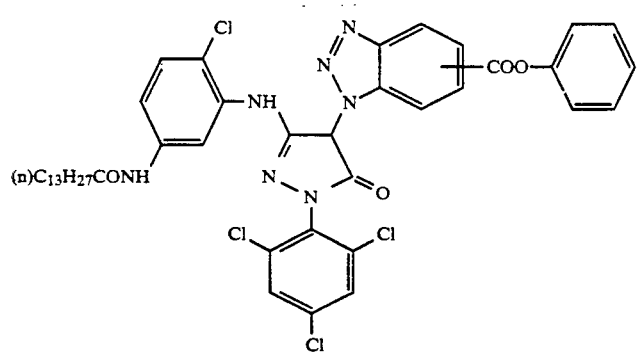
ExM-2
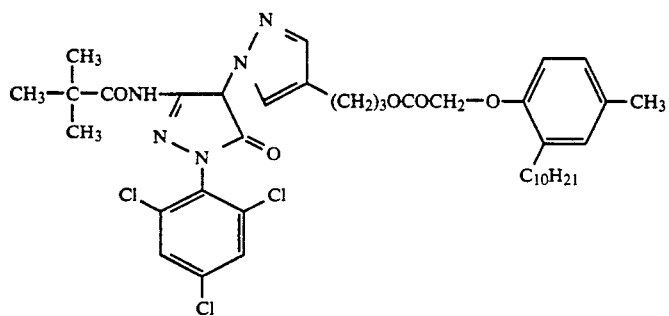
ExM-4

-continued
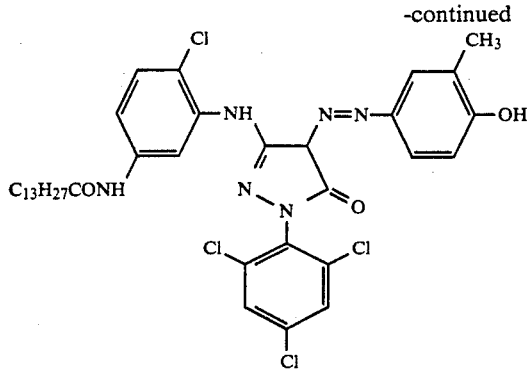 ExM-5
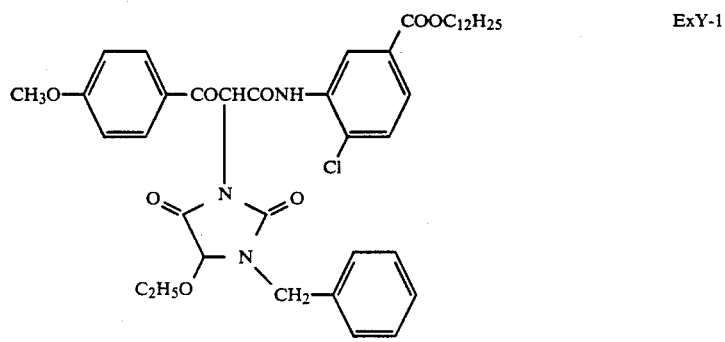 ExY-1
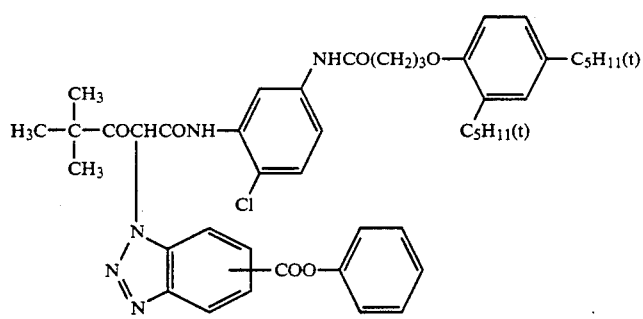 ExY-2
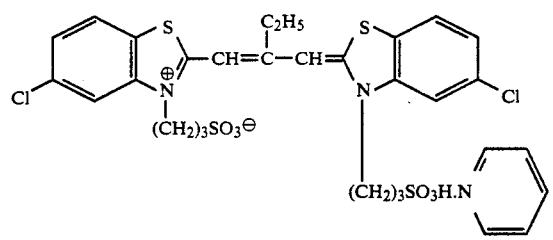 ExS-1
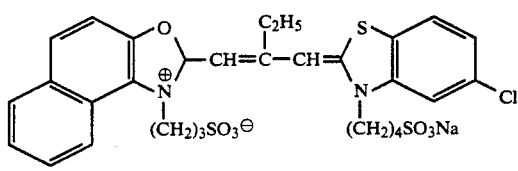 ExS-2
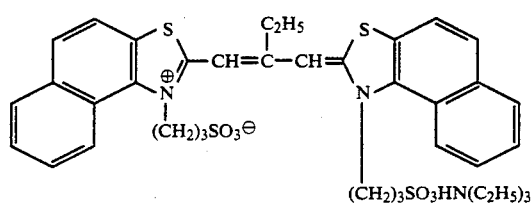 ExS-3

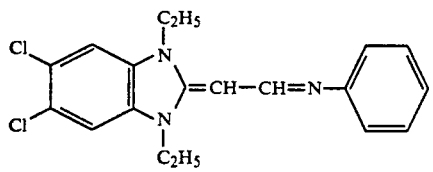
ExS-4
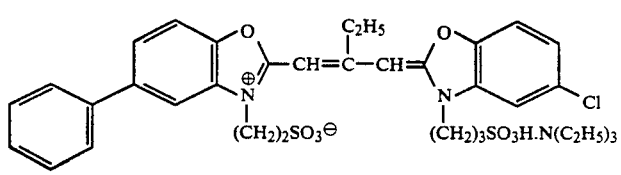
ExS-5
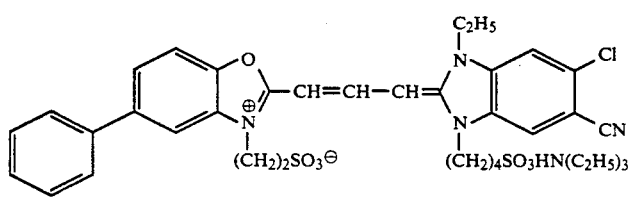
ExS-6
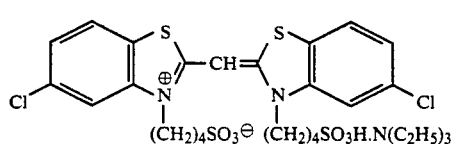
ExS-8
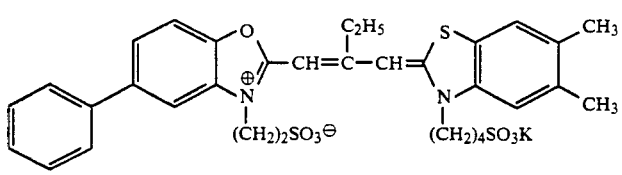
ExS-7
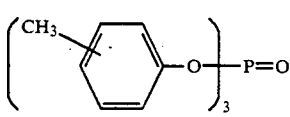
Solv-1
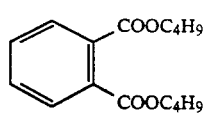
Solv-2
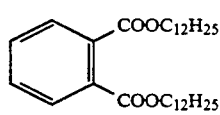
Solv-3
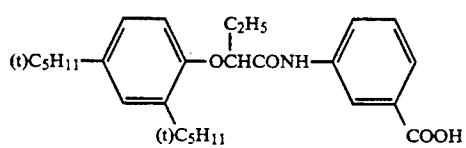
Solv-5
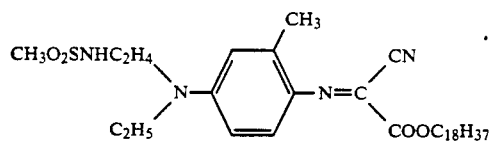
Cpd-1

-continued

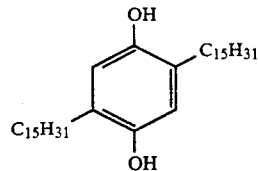
Cpd-2

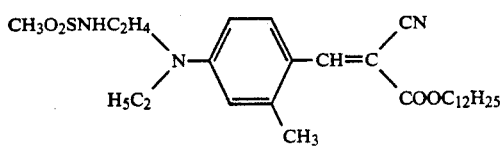
Cpd-3

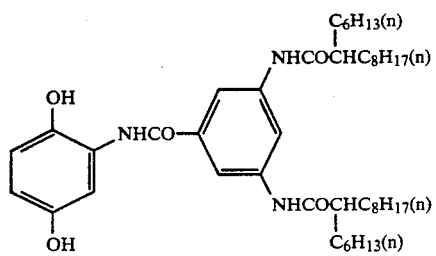
Cpd-4

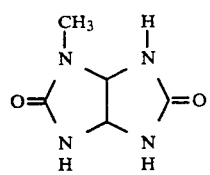
Cpd-5

$C_8H_{17}SO_2NHCH_2CH_2CH_2OCH_2CH_2N^{\oplus}(CH_3)_3$  W-1

$$CH_2=CHSO_2CH_2CONH-CH_2$$
$$CH_2=CHSO_2CH_2CONH-CH_2$$
H-1

The color light-sensitive material thus-prepared was subjected to development processing as described in Example 1, development processing as described in Example 2, or development processing using an automatic developing machine according to the following processing steps.

| Processing Step | Processing Temperature (°C.) | Processing Time | Amount of* Replenishment (ml) | Capacity of Tank (l) |
|---|---|---|---|---|
| Color Development | 37.8 | 3 min. 15 sec. | 21 | 5 |
| Bleaching | 38.0 | 45 sec. | 4.5 | 2 |
| Fixing (1) | 38.0 | 45 sec. | Two-tank countercurrent system | 2 |
| Fixing (2) | 38.0 | 45 sec. | 30 | 2 |
| Stabilizing (1) | 38.0 | 20 sec. | Three-tank countercurrent system | 1 |
| Stabilizing (2) | 38.0 | 20 sec. |  | 1 |
| Stabilizing (3) | 38.0 | 20 sec. | 35 | 1 |
| Drying | 55 | 1 min. 00 sec. | | |

*Amount of replenishment per meter of 35 m/m width strip

In the fixing tank of the automatic developing machine used, a jet stirrer as described in JP-A-62-183460, page 3 was equipped, and the light-sensitive material was processed in a manner such that the jet of the fixing solution struck the surface of the light-sensitive material.

The composition of each processing solution used is illustrated below.

| | Tank Solution | Replenisher |
|---|---|---|
| Color Developing Solution: | | |
| Diethylenetriaminepentaacetic Acid | 5.0 g | 6.0 g |
| Sodium Sulfite | 4.0 g | 5.0 g |
| Potassium Carbonate | 30.0 g | 37.0 g |
| Potassium Bromide | 1.3 g | 0.5 g |
| Potassium Iodide | 1.2 mg | — |
| Hydroxylamine Sulfate | 2.0 g | 3.6 g |
| 4-[N-Ethyl-N-β-hydroxyethyl-amino]-2-methylaniline Sulfate | 4.7 g | 6.2 g |
| Water to make | 1.0 l | 1.0 l |
| pH | 10.00 | 10.15 |
| Bleaching Solution: | | |
| Ferric Complex of 1,3-Diamino-propanetetraacetic Acid | 130 g (0.36 mol/l) | 190 g (0.53 mol/l) |
| 1,3-Diaminopropanetetraacetic Acid | 3.0 g | 4.0 g |
| Ammonium Bromide | 85 g | 120 g |
| Acetic Acid | 50 g | 70 g |
| Ammonium Nitrate | 30 g | 40 g |
| Water to make | 1.0 l | 1.0 l |
| pH | 4.3 | 3.5 |

The pH was adjusted with acetic acid and aqueous ammonia.

| Fixing Solution: | Tank Solution | Replenisher |
|---|---|---|
| 1-Hydroxyethylidene-1,1-diphosphonic Acid | 5.0 g | 7.0 g |
| Disodium Ethylenediaminetetraacetate | 0.5 g | 0.7 g |
| Sodium Sulfite | 10.0 g | 12.0 g |
| Sodium Bisulfite | 8.0 g | 10.0 g |
| Aqueous Solution of Ammonium Thiosulfate (700 g/l) | 170.0 ml | 200.0 ml |
| Ammonium Thiocyanate | 100.0 g | 150.0 g |
| Thiourea | 3.0 g | 5.0 g |
| 3,6-Dithia-1,8-octanediol | 3.0 g | 5.0 g |
| Water to make | 1.0 l | 1.0 l |
| pH | 6.5 | 6.7 |

The pH was adjusted with acetic acid and aqueous ammonia.

| Stabilizing Solution: (both tank solution and replenisher) | |
|---|---|
| Formaldehyde (37% aq. soln.) | 1.2 ml |
| 5-Chloro-2-methyl-4-isothiazolin-3-one | 6.0 mg |
| 2-Methyl-4-isothiazolin-3-one | 3.0 mg |
| Surface Active Agent $C_{10}H_{21}-O-(CH_2CH_2O)_{10}-H$ | 0.4 g |
| Ethylene Glycol | 1.0 g |
| Water to make | 1.0 l |
| pH | 5.0 to 7.0 |

It was found that Sample 301 exhibited excellent color reproducibility and sharpness using any of the development processings.

While the invention has been described in detail and with reference to specific embodiments thereof, it will be apparent to one skilled in the art that various changes and modifications can be made therein without departing from the spirit and scope thereof.

What is claimed is:

1. A silver halide color photographic material comprising a support having thereon at least one silver halide emulsion layer, wherein the silver halide color photographic material contains a compound represented by the following general formula (II):

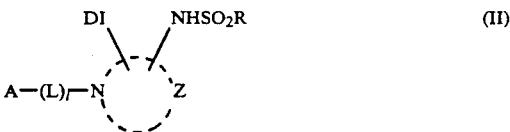

wherein A represents a group whose bond to $(L)_l$—N is capable of being cleaved upon reaction with an oxidation product of a developing agent; L represents a group whose bond to a 5-membered, 6-membered or 7-membered nitrogen-containing unsaturated heterocyclic group which has 2 to 6 carbon atoms, is capable of being cleaved after being cleaved from A; Z represents a group of atoms necessary to complete a 5-membered, 6-membered or 7-membered nitrogen-containing unsaturated heterocyclic group which has 2 to 6 carbon atoms, which heterocyclic group is connected to $A—(L)_l$ at the nitrogen atom, and which has a sulfonamido group and a development inhibitor group or a precursor thereof on the ring carbon atoms; DI represent a development inhibitor group and DI is connected to a carbon atom of the heterocyclic ring containing Z through a hetero atom included therein; R represents a substituent; and the sulfonamido group is connected to a carbon atom of the heterocyclic ring containing Z, provided that the nitrogen atom at which $A—(L)_l$ is connected and the nitrogen atom in the sulfonamido group are positioned so as to satisfy the Kendall-Pelz rule; l represents an integer of 0 to 2, and when l represents 2, the two L's may be the same or different.

2. A silver halide color photographic material as claimed in claim 1, wherein A is a coupler residue or an oxidation-reduction group capable of releasing

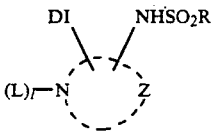

upon oxidation.

3. A silver halide color photographic material as claimed in claim 1, wherein L is a timing group or a linking group.

4. A silver halide color photographic material as claimed in claim 2, wherein the coupler residue represented by A is a yellow coupler residue, a magenta coupler residue, a cyan coupler residue or a non-color forming coupler residue.

5. A silver halide color photographic material as claimed in claim 2, wherein the coupler residue represented by A is selected from the group consisting of an acylacetanilide coupler residue, a malondianilide coupler residue, a 5-pyrazolone coupler residue, a pyrazolotriazole coupler residue, a pyrazoloimidazole coupler residue, a phenol coupler residue, a naphthol coupler residue, an imidazole coupler residue, an indanone coupler residue and an acetophenone coupler residue.

6. A silver halide color photographic material as claimed in claim 2, wherein A represents a coupler residue represented by the following general formula (Cp-1), (Cp-2), (Cp-3), (Cp-4), (Cp-5), (Cp-6), (Cp-7), (Cp-8), (Cp-9) or (Cp-10):

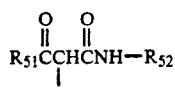 (Cp-1)

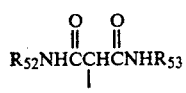 (Cp-2)

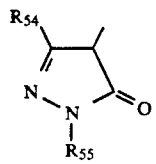 (Cp-3)

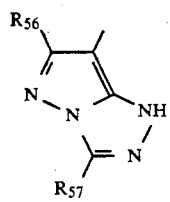 (Cp-4)

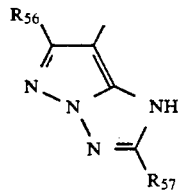 (Cp-5)

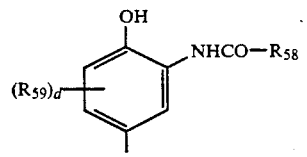 (Cp-6)

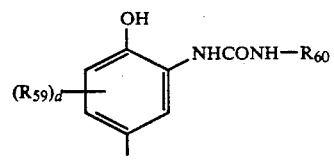 (Cp-7)

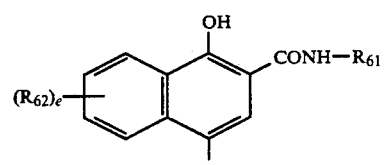 (Cp-8)

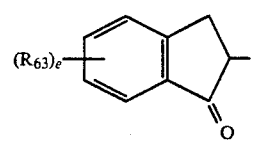 (Cp-9)

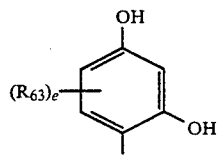 (Cp-10)

wherein $R_{41}$ represents an aliphatic group, an aromatic group or heterocyclic group; $R_{42}$ represents an aromatic group or a heterocyclic group; and $R_{43}$, $R_{44}$ and $R_{45}$ each represents a hydrogen atom, an aliphatic group, an aromatic group or a heterocyclic group;

$R_{51}$ represents a group as defined for $R_{41}$;

$R_{52}$ and $R_{53}$ each represents a group as defined for $R_{42}$;

$R_{54}$ represents a group as defined for $R_{41}$, a group

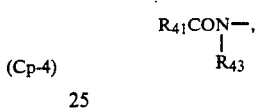

a group

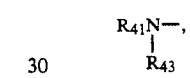

a group

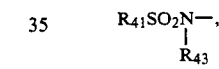

a group $R_{41}S-$, a group $R_{43}O-$, a group

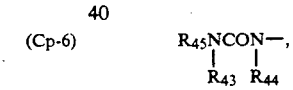

or a group $N\equiv C-$;

$R_{55}$ represents a group as defined for $R_{41}$;

$R_{56}$ and $R_{57}$ each represents a group as defined for $R_{43}$, a group $R_{41}S-$, a group $R_{43}O-$, a group

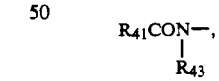

or a group

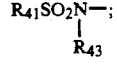

$R_{58}$ represents a group as defined for $R_{41}$;

$R_{59}$ represents a group as defined for $R_{41}$, a group

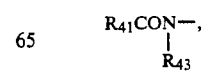

a group a group

a group

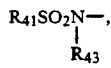

a group

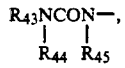

a group R$_{41}$O—, a group R$_{41}$S—, a halogen atom or a group

d represents an integer from 0 to 3, and when d represents 2 or more, the two or more R$_{59}$'s may be the same or different, or each of the two R$_{59}$'s may be a divalent group and connected with each other to form a cyclic structure;

R$_{60}$ represents a group as defined for R$_{41}$;

R$_{61}$ represents a group as defined for R$_{41}$;

R$_{62}$ represents a group as defined for R$_{41}$, a group R$_{41}$CONH—, a group R$_{41}$OCONH—, a group R$_{41}$SO$_2$NH—, a group

a group

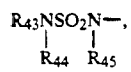

a group R$_{43}$O—, a group R$_{41}$S—, a halogen atom or a group

R$_{63}$ represents a group as defined for R$_{41}$, a group

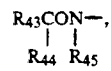

a group

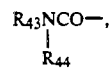

a group

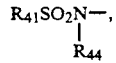

a group

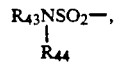

a group R$_{41}$SO$_2$—, a group R$_{43}$OCO—, a group R$_{43}$OSO$_2$—, a halogen atom, a nitro group, a cyano group or a group R$_{43}$CO—; and e represents an integer from 0 to 4, and when e is 2 or more, the two or more R$_{62}$'s or R$_{63}$'s may be the same or different.

7. A silver halide color photographic material as claimed in claim 6, wherein the substituent for the aliphatic group, aromatic group or heterocyclic group is selected from the group consisting of a halogen atom, a group R$_{47}$O—, a group R$_{46}$S—, a group

a group

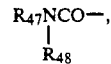

a group

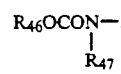

a group

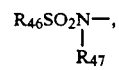

a group

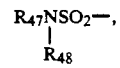

a group R$_{46}$SO$_2$—, a group R$_{47}$OCO—, a group

a group as defined for R$_{46}$, a group

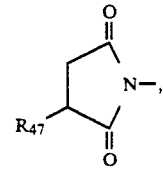

a group $R_{46}COO-$, a group $R_{47}OSO_2-$, a cyano group, or a nitro group, wherein $R_{46}$ represents an aliphatic group, an aromatic group or a heterocyclic group; and $R_{47}$, $R_{48}$ and $R_{49}$ each represents a hydrogen atom, an aliphatic group, an aromatic group or a heterocyclic group.

8. A silver halide color photographic material as claimed in claim 6, wherein $R_{51}$ represents an aliphatic group or an aromatic group; $R_{52}$, $R_{53}$ and $R_{55}$ each represents an aromatic group; $R_{54}$ represents a group $R_{41}CONH-$ or a group

$R_{56}$ and $R_{57}$ each represents an aliphatic group, a group $R_{41}O-$ or a group $R_{41}S-$; $R_{58}$ represents an aliphatic group or an aromatic group; $R_{59}$ in the general formula (Cp-6) represents a chlorine atom, an aliphatic group or a group $R_{41}CONH-$; d in the general formula (Cp-6) represents 1 or 2; $R_{60}$ represents an aromatic group; $R_{59}$ in the general formula (Cp-7) represents a group $R_{41}CONH-$; d in the general formula (Cp-7) represents 1; $R_{61}$ represents an aliphatic group or an aromatic group; e in the general formula (Cp-8) represents 0 or 1; $R_{62}$ represents a group $R_{41}OCONH-$, a group $R_{41}CONH-$ or a group $R_{41}SO_2NH-$; $R_{63}$ in the general formula (Cp-9) represents a group $R_{41}CONH-$, a group $R_{41}SO_2NH-$, a group

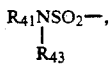

a group $R_{41}SO_2-$, a group

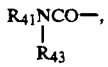

a nitro group or a cyano group; and $R_{63}$ in the general formula (Cp-10) represents a group

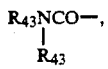

or a group $R_{43}CO-$.

9. A silver halide color photographic material as claimed in claim 1, wherein L is connected to A through an oxygen atom, a sulfur atom or a nitrogen atom included therein.

10. A silver halide color photographic material as claimed in claim 9, wherein L is a methyleneoxy group, a 4-methylene-3-pyrazolyloxy group, a 2-methylenephenoxy group, a 4-methylenephenoxy group or a 2-carbonylaminomethylphenoxy group.

11. A silver halide color photographic material as claimed in claim 1, wherein the substituent represented by R is an aliphatic group, an aromatic group, a heterocyclic group, an aliphatic oxy group or an amino group.

12. A silver halide color photographic material as claimed in claim 1, wherein the heterocyclic ring formed by Z together with the nitrogen atom is a pyrrole ring, an imidazole ring, a pyrazole ring, an 1,2,4-triazole ring, an indole ring or an α-pyridone ring.

13. A silver halide color photographic material as claimed in claim 1, wherein the development inhibitor group represented by DI is a heterocyclic thio group or a nitrogen-containing heterocyclic group connected through the nitrogen atom.

14. A silver halide color photographic material as claimed in claim 1, wherein the compound represented by the general formula (II) is a compound represented by the following general formula (III):

wherein A, L, l DI and R each has the same meaning as in formula (II); one of $Z_1$, $Z_2$, $Z_3$ and $Z_4$ represents a carbon atom connected to DI; one of $Z_1$, $Z_2$, $Z_3$ and $Z_4$ other than the methine group connected to DI represents a carbon atom connected to $NHSO_2R$; and the two remaining of $Z_1$, $Z_2$, $Z_3$ and $Z_4$ each represents a substituted or unsubstituted methine group or a nitrogen atom.

15. A silver halide color photographic material as claimed in claim 14, wherein the methine group represented by $Z_1$, $Z_2$, $Z_3$ or $Z_4$ is substituted with an aliphatic group, an aromatic group, a halogen atom, an alkoxy group, an alkylthio group, an aromatic thio group, a sulfonyl group, an alkoxycarbonyl group, an acylamino group, an acyl group, a carbamoyl group, a ureido group, a sulfamoyl group, an amino group, a sulfonamido group or a carboxy group.

16. A silver halide color photographic material as claimed in claim 1, wherein the silver halide color photographic material comprises at least one red-sensitive silver halide emulsion layer, at least one green-sensitive silver halide emulsion layer and at least one blue-sensitive silver halide emulsion layer.

17. A silver halide color photographic material as claimed in claim 16, wherein at least one of the red-sensitive silver halide emulsion layers contains at least one cyan color forming coupler, at least one of the green-sensitive silver halide emulsion layers contains at least one magenta color forming coupler and at least one of the blue sensitive silver halide emulsion layers contains at least one yellow color forming coupler.

18. A silver halide color photographic material as claimed in claim 1, wherein the amount of compound of the formula (I) is in the range from $1 \times 10^{-6}$ mol to 0.5 mol per mol of silver present in the same layer containing the compound of the formula (I) or a layer adjacent thereto.

19. A silver halide color photographic material as claimed in claim 1, wherein silver halide in the silver halide emulsion layer is silver iodobromide, silver iodochloride or silver iodochlorobromide each containing about 30 mol % or less of silver iodide.

* * * * *